US011714202B2

(12) United States Patent
Maolinbay

(10) Patent No.: US 11,714,202 B2
(45) Date of Patent: Aug. 1, 2023

(54) HIGH RESOLUTION DYNAMIC DETECTOR FOR IMAGING AND DOSIMETRY IN MEGAVOLTAGE RADIATION THERAPY

(71) Applicant: RefleXion Medical, Inc., Hayward, CA (US)

(72) Inventor: Manat Maolinbay, Gilroy, CA (US)

(73) Assignee: RefleXion Medical, Inc., Hayward, CA (US)

( * ) Notice: Subject to any disclaimer, the term of this patent is extended or adjusted under 35 U.S.C. 154(b) by 0 days.

(21) Appl. No.: 17/711,606

(22) Filed: Apr. 1, 2022

(65) Prior Publication Data
US 2022/0326402 A1    Oct. 13, 2022

Related U.S. Application Data

(60) Continuation of application No. 16/993,029, filed on Aug. 13, 2020, now Pat. No. 11,300,692, which is a division of application No. 15/921,219, filed on Mar. 14, 2018, now Pat. No. 10,775,517, which is a continuation of application No. PCT/US2016/051750, filed on Sep. 14, 2016.

(60) Provisional application No. 62/218,425, filed on Sep. 14, 2015.

(51) Int. Cl.
| | |
|---|---|
| *G01T 1/20* | (2006.01) |
| *G01T 1/24* | (2006.01) |
| *G01T 1/29* | (2006.01) |
| *G01T 3/06* | (2006.01) |
| *A61N 5/10* | (2006.01) |
| *G01T 7/00* | (2006.01) |

(52) U.S. Cl.
CPC .......... *G01T 1/2018* (2013.01); *A61N 5/1049* (2013.01); *G01T 1/201* (2013.01); *G01T 1/24* (2013.01); *G01T 1/29* (2013.01); *G01T 3/06* (2013.01); *G01T 7/005* (2013.01)

(58) Field of Classification Search
CPC ....... G01T 1/2018; G01T 1/201; G01T 7/005; G01T 1/24; G01T 3/06; G01T 1/29; A61N 5/1049
See application file for complete search history.

(56) References Cited

U.S. PATENT DOCUMENTS

| | | | |
|---|---|---|---|
| 3,794,840 A | | 2/1974 | Scott |
| 5,636,299 A | | 6/1997 | Bueno |
| 5,784,432 A | * | 7/1998 | Kurtz ............... G01N 23/20 378/70 |
| 5,864,146 A | | 1/1999 | Karellas |
| 5,886,783 A | | 3/1999 | Shapanus |
| 8,610,077 B2 | | 12/2013 | Beaulieu et al. |
| 9,242,120 B2 | | 1/2016 | Verhaegen et al. |
| 9,265,971 B2 | | 2/2016 | Baltes |
| 9,364,186 B2 | | 6/2016 | Nioutslkou |
| 9,770,603 B2 | | 9/2017 | Da Silva Rodrigues et al. |
| 10,775,517 B2 | | 9/2020 | Maolinbay |
| 11,300,692 B2 | | 4/2022 | Maolinbay |
| 2009/0014662 A1 | | 1/2009 | Suhami |

OTHER PUBLICATIONS

Blake, S.J. et al. (2013). "Characterization of a novel EPID designed for simultaneous imaging and dose verification in radiotherapy," *Med. Phys.* 40:091902-1-091902-11.
International Search Report dated Jan. 6, 2017, for PCT Application No. PCT/US2016/051750, filed on Sep. 14, 2016, 4 pages,.
Mijnheer, B. et al. (2013). 3D EPID-based in vivo dosimetry for IMRT and VMAT, 7th International Conference on 3D Radiation Dosimetry (IC3DDose), IOP Publishing, J. Physics: Conference Series 444, pp. 1-7.
Non-Final Office Action dated Aug. 27, 2019, for U.S. Appl. No. 15/921,219, filed Mar. 14, 2018, 17 pages.
Non-Final Office Action dated Jun. 14, 2021, for U.S. Appl. No. 16/993,029, filed Aug. 13, 2020, 12 pages.
Notice of Allowance dated May 27, 2020, for U.S. Appl. No. 15/921,219, filed Mar. 14, 2018, 9 pages.
Notice of Allowance dated Dec. 16, 2021, for U.S. Appl. No. 16/993,029, filed Aug. 13, 2020, 9 pages.
Ruchti, R.C. (1996). "The use of scintillating fibers for charged-particle tracking," *Annu. Rev. Nucl. Part. Sci.* 46:261-319.
Star-Lack, J. et al. (2015). "A piecewise-focused high DQE detector for MV imaging," *Med. Phys.* 42:5084-5099.
Steciw, S. et al. (2005). "Three-dimensional IMRT verification with a flat-panel EPID," *Med. Phys.* 32:600-612.
Teymurazyan, A. et al. (2012). "Monte Carlo simulation of a novel water-equivalent electronic portal imaging device using plastic scintillating fibers," *Med. Phys.* 39:1518-1529.
Wang, Y. et al. (2009). "High-DQE EPIDs based on thick, segmented BGO and CsI:TI scintillators: 25 performance evaluation at extremely low dose," *Med. Phys.* 36:5707-5718.
Wendling, M. et al. (2006). "Accurate two-dimensional IMRT verification using a back-projection EPID dosimetry method," *Med. Phys.* 33:259-273.

(Continued)

*Primary Examiner* — David P Porta
*Assistant Examiner* — Meenakshi S Sahu
(74) *Attorney, Agent, or Firm* — Cooley LLP

(57) ABSTRACT

Disclosed herein are variations of megavoltage (MV) detectors that may be used for acquiring high resolution dynamic images and dose measurements in patients. One variation of a MV detector comprises a scintillating optical fiber plate, a photodiode array configured to receive light data from the optical fibers, and readout electronics. In some variations, the scintillating optical fiber plate comprises one or more fibers that are focused to the radiation source. The diameters of the fibers may be smaller than the pixels of the photodiode array. In some variations, the fiber diameter is on the order of about 2 to about 100 times smaller than the width of a photodiode array pixel, e.g., about 20 times smaller. Also disclosed herein are methods of manufacturing a focused scintillating fiber optic plate.

17 Claims, 19 Drawing Sheets

(56) References Cited

OTHER PUBLICATIONS

Written Opinion of the International Searching Authority dated Jan. 6, 2017, for PCT Application No. PCT/US2016/051750, filed on Sep. 14, 2016, 6 pages.

* cited by examiner

| Table 1. Tile angles along X direction, tile width 5.5cm | | | | | | | | |
|---|---|---|---|---|---|---|---|---|
| TILE NUMBER | 1 | 2 | 3 | 4 | 5 | 6 | 7 | 8 |
| FIBER TILT ANGLE (DEG.) | 1.19 | 3.56 | 5.92 | 8.27 | 10.58 | 12.86 | 15.10 | 17.29 |
| DISTANCE TO TILE CENTER (CM) | 2.75 | 8.250 | 13.750 | 19.250 | 24.750 | 30.250 | 35.750 | 41.250 |
| TILE CUT ANGLE (DEG.) | 2.38 | 4.75 | 7.10 | 9.43 | 11.73 | 13.99 | 16.20 | 18.37 |
| DISTANCE TO TILE EDGE (CM) | 5.500 | 11.000 | 16.500 | 22.000 | 27.500 | 33.000 | 38.500 | 44.000 |

| Table 2. Tile angles along Z direction. Tile width 2.66cm | | | |
|---|---|---|---|
| Tile number | 1 | 2 | 3 |
| Fiber Tilt Angle (deg.) | 1.15 | 0.00 | 1.15 |
| Distance to Tile Center (cm) | 2.66 | 0.000 | 2.660 |
| Tile Cut Angle (deg.) | 1.73 | 0.58 | 1.73 |
| Distance to Tile Edge (cm) | 4.000 | 1.330 | 4.000 |

| Table 3. Example parameters | |
|---|---|
| Number of firing position per rotation | 100 |
| Gantry rotations per second | 1 |
| Beam Width (mm) | 10 |
| Couch speed (mm/s) | 0.07 |
| Couch distance per treatment (mm) | 100 |
| Number of images in total | 142857 |
| Overlap factor | 143 |
| Number of images after averaging | 1000 |

FIG. 11A

HIGH RESOLUTION DYNAMIC DETECTOR FOR IMAGING AND DOSIMETRY IN MEGAVOLTAGE RADIATION THERAPY

CROSS-REFERENCE TO RELATED APPLICATIONS

This application is a continuation of U.S. application Ser. No. 16/993,029, filed Aug. 13, 2020, which is a divisional of U.S. application Ser. No. 15/921,219, filed on Mar. 14, 2018, now U.S. Pat. No. 10,775,517, which is a continuation of International Application No. PCT/US2016/051750, filed on Sep. 14, 2016, which claims priority to U.S. Provisional Patent Application Ser. No. 62/218,425, filed on Sep. 14, 2015, each of which are hereby incorporated by reference in their entirety.

BACKGROUND

In modern megavoltage (MV) X-ray radiation therapy, the radiation detector used to determine the position of the patient within the therapy system is typically different from the detector used to measure the radiation dose delivered to that patient during the therapy session. One reason that two separate detectors are used is that the sensitivity of the detector for anatomical imaging is different from the sensitivity of the detector for measuring radiation dosage. Detectors suitable for anatomical imaging, such as electronic portal imaging detectors (EPID), often use scintillating materials made of heavy elements, such as Gadolinium oxysulfide (GOS) or cesium iodide doped with thallium (CsI(Tl)). However, because such materials have a radiation dose response which is vastly different from tissue or water, they are not suitable for patient dosimetry measurements. Detectors suitable for measuring the radiation dose delivered to a patient are typically made of a low-Z material, which have a similar radiation dose response to that of tissue or water. Examples may include dry air in ion chambers, diamond, silicon, etc. Such detectors are not appropriate for acquiring images because of their low stopping power for X-rays. Although increasing the thickness of the low-Z material may allow for the capture of more X-rays, the resultant image may have poor spatial resolution.

Accordingly, a radiation detection system that is capable of both acquiring images at a useful spatial resolution and measuring the radiation dose delivered to a patient is desirable.

BRIEF SUMMARY

Disclosed herein is a megavoltage (MV) detector that may be used for acquiring high resolution dynamic images and dose measurements in patients. One variation of a MV detector may comprise a light photon converter, a light sensor array (e.g., a photodiode array), and optical fibers optically connecting the photon converter and photodiode array. In some variations, a MV detector may comprise optical fibers configured to convert X-rays into photons (e.g., scintillating optical fibers) and act as a light guide or channel to deliver the photons to a light sensor array. For example, a MV detector may comprise a scintillating fiber optic plate coupled to an array of photodiodes and thin-film transistors (TFT), where each photodiode and TFT pair represents a pixel of an image. The scintillating fiber optic plate may comprise a plurality of micron-sized optical fibers bundled together, and the fibers may be angled such that they are aligned along the rays of an X-ray source located across from the MV detector (i.e., the fibers of the scintillating fiber optic plate are "focused" to the X-ray source). The fibers may be made of a low-Z material (e.g., plastic). In some variations, the fibers of a focused scintillating fiber optic plate (FSFOP) may be clustered into groups, for example, a left cluster (or block, or module) of fibers and a right cluster (or block or module) of fibers. FSFOPs may have a thickness, which may correspond to the length of the fibers, from about 1.5 cm to about 30 cm, e.g., about 5 cm thick, e.g., about 4 cm thick. The diameters of the fibers may be smaller than the pixels of the photodiode array. In some variations, the fiber diameter may be on the order of about 2 to about 100 times smaller than the width of a photodiode array pixel, e.g., about 20 times smaller. Also disclosed herein are methods of manufacturing MV detectors that comprise a FSFOP and a photodiode/TFT array and methods of using the MV detectors described herein to both generate a patient image and to determine the amount and location of radiation (i.e., the radiation dose) emitted by a source and/or applied to the patient during a radiation therapy treatment session.

One variation of a radiation detector may comprise a fiber optic array comprising a plurality of scintillating fibers, each fiber having a diameter, an input face, an output face, and a longitudinal axis therebetween, and a photodiode array coupled to the output faces of the fibers in the array. The fibers may be focused to a radiation source. The photodiode array may comprise a plurality of photodiodes representing a plurality of pixels, where each pixel has a pixel width. The fiber diameter may be smaller than the pixel width and a plurality of the output faces of a plurality fibers may be in contact with each pixel of the photodiode array. In some variations, each pixel of the photodiode array may directly contact a plurality of fibers. The longitudinal axis of each fiber may be aligned with a propagation axis of a ray of radiation emanating from the radiation source, and/or the longitudinal axes of the fibers may be aligned to rays of a radiation beam emitted by the radiation source. The fiber optic array may have a thickness from about 1.5 cm to about 5 cm. The ratio of the fiber diameter to the pixel width may be from about 1:10 to about 1:100. The fiber diameter may be from about 5 µm to about 10 µm (e.g., about 10 µm), and the pixel width may be from about 150 µm to about 1000 µm (e.g., about 400 µm). The scintillating fibers may comprise a material having a density similar to that of water, e.g., about 1 g/cm$^3$, or about about 1.18 g/cm$^3$. For example, the material may be a plastic. In some variations, the plurality of scintillating fibers may be clustered in blocks, where the fibers of each fiber block may be aligned to a unique or different portion of the radiation source beam. The radiation source may emit a fan beam having a right portion and a left portion, and the fiber optic array may comprise a first block of scintillating fibers aligned toward the right portion of the fan beam and a second block of scintillating fibers aligned toward the left portion of the fan beam. In some variations, a radiation detector may comprise a sheet of metal between each of the blocks. The metal may comprise a high-Z metal, and may have a thickness from about 0.1 mm to about 2 mm.

In some variations, the fiber optic array may comprise a top surface having a first surface area and a bottom surface having a second surface area, where the first surface area is less than the second surface area and the bottom surface contacts the photodiode array. Optionally, a metal sheet may be disposed over the top surface of a fiber optic array. The metal sheet may be a low-Z metal, such as copper or aluminum. The metal sheet may have a thickness from about 0.05 mm to about 1 mm, e.g., about 0.2 mm. Alternatively or additionally, a fiber optic array may comprise a top surface and a bottom surface that contacts the photodiode array, where the top surface may be coated with one of a light-reflective paint or a light-absorbing paint.

Disclosed herein is one variation of a method of manufacturing an optical fiber plate for a detector. One method may comprise providing a block of parallel scintillating optical fibers, slicing the block along a first axis that transects the optical fibers at a first angle with respect to the parallel fibers to create a top surface, slicing the block along a second axis that transects the optical fibers at a first distance away from the top surface to create a bottom surface, wherein the bottom surface is parallel to the top surface, slicing the block along a third axis to create a first side surface that is at a second angle with respect to the top surface, slicing the block along a fourth axis at a second distance away from the third axis to create a second side surface, wherein the second side surface is at a third angle with respect to the top surface. The first distance may correspond to a thickness of an optical fiber plate and the second distance may correspond to a width of the optical fiber plate. The third angle may be different from the second angle, and/or the first angle may be from about 10 degrees to about 180 degrees, and/or the second and third angles are from about 0.5 degrees to about 40 degrees. The scintillating fiber located at the center of the optical fiber plate may be at a fourth angle such that the center scintillating fiber is aligned with a ray of a radiation source fan beam located at a fixed distance away from the optical fiber plate. The method may further comprise comprising slicing the block along a fifth axis to create a third side surface and a sixth axis at a third distance away from the fifth axis to create a fourth side surface, where the third side surface is at a fourth angle with respect to the top surface and the fourth side surface is at a fifth angle with respect to the top surface. The scintillating optical fibers may comprise plastic scintillating optical fibers, and/or may have diameters from about 5 µm to about 10 µm.

Another method of manufacturing an optical fiber plate may comprise providing a billet of tapered scintillating optical fibers, slicing the billet along a first axis that transects all of the fibers to create a top surface, slicing the billet along a second axis that transects all of the fibers at a first distance away from the first cut to create a bottom surface, wherein the bottom surface is parallel to the top surface, slicing the billet along a third axis to create a first side surface that is at a first angle with respect to the top surface, and slicing the billet along a fourth axis at a second distance away from the third axis to create a second side surface that is at a second angle with respect to the top surface. The billet of scintillating optical fibers may be thermally tapered. The taper angle of the billet of optical fibers may be determined at least in part by the shape of a radiation beam from a radiation source that is to be located at a fixed distance away from the optical fiber plate. The first side surface may extend along a length of a first boundary fiber in the tapered billet, and the second side surface may extend along a length of a second boundary fiber in the tapered billet. The scintillating optical fibers may comprise plastic scintillating optical fibers, and/or may have diameters from about 5 µm to about 10 µm.

Another variation of a radiation detector may comprise an optical fiber plate comprising a matrix of optical fiber modules, wherein each optical fiber module comprises a plurality of scintillating optical fibers including a central scintillating optical fiber located in the center of each fiber module, and a photodiode array coupled to a bottom surface of the optical fiber plate, the photodiode array comprising a plurality of photodiodes representing a plurality of pixels, each pixel having a pixel width. The central scintillating optical fiber of each of the optical fiber modules may be focused to a radiation source to be located at a fixed distance away from the radiation detector. The radiation detector may optionally comprise opaque septa between each of the optical fiber modules. The longitudinal axis of the central scintillating optical fiber of each of the optical fiber modules may be aligned along a ray of a radiation beam generated by the radiation source. A longitudinal axis of each of the optical fibers in each of the modules may be aligned along different rays of the radiation beam. Alternatively or additionally, the longitudinal axis of the central scintillating fiber of each of the plurality of fiber modules may be aligned with a different ray of the radiation beam. The optical fiber plate has a thickness from about 1.5 cm to about 5 cm. The optical fiber plate further comprises a low-Z metal plate disposed over a top surface of the plate. In some variations, the area of the bottom surface of the optical fiber plate may be greater than the area of a top surface of the optical fiber plate. The fiber diameter may be smaller than the pixel width and a plurality of output faces of the fibers may be in contact with each pixel of the photodiode array. The scintillating optical fibers may comprise plastic scintillating optical fibers. The scintillating optical fibers have a diameter from about 5 µm to about 10 µm. In some variations, the scintillating optical fibers may comprise materials having different refractive indices.

BRIEF DESCRIPTION OF THE DRAWINGS

FIG. 11A depicts Table 3, which summarizes example parameters (e.g., rates of rotation and movement) for one variation of a treatment session.

FIG. 13 is a graphical representation of the number of images available for averaging as a function of couch displacement for one variation of a radiation therapy system.

DETAILED DESCRIPTION

Figure 1B:
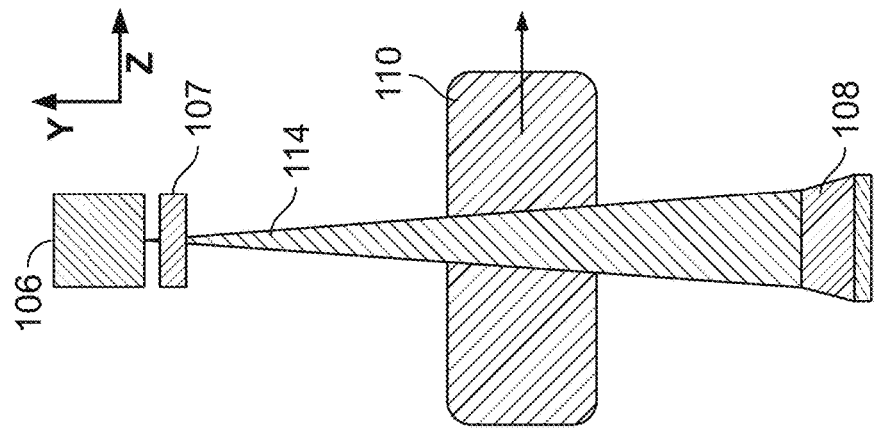
FIG. 1B is a side view of a portion of the system of FIG. 1A.

A radiation therapy system may comprise a patient area, a radiation source located on one side of the patient area configured to apply radiation to a patient, and a MV detector located on a second side of the patient area (e.g., generally opposite the radiation source) configured to detect radiation from the source. The readings from the MV detector may be used to generate an image of a patient, and/or may be used to compute the radiation dose delivered to the patient from the radiation source. However, MV detectors that are suitable for detecting radiation for the purpose of generating a high-resolution anatomical image are not usually suitable for measuring the radiation dose applied to the patient. For example, an MV detector for anatomical imaging may comprise a layer of hi-Z material, but since a hi-Z material has a radiation dose response that is different from the radiation dose response of tissue or water, it may be computationally challenging or intensive to determine the dose delivered to the patient. MV detectors suitable for measuring radiation dosage are usually not suitable for generating high resolution anatomical images. MV detectors for dosimetry purposes usually comprise a layer of low-Z material (e.g., having a similar or equivalent response to human tissue and/or water) which facilitates the radiation dose computations, but does not provide enough stopping power to capture X-rays for anatomical imaging.

Disclosed herein are novel MV detectors for high resolution dynamic imaging and dose measurement. These MV detectors may be used in a radiation therapy system in order to provide the practitioner with information about the anatomy and/or position of the patient, as well as the radiation dose delivered to a particular location in the patient during a radiotherapy treatment session. Also disclosed herein are methods of manufacturing such MV detectors. One variation of a detector may comprise a fiber optic plate, a light sensor array such as a photodiode array (i.e., a photodiode/TFT array), and readout electronics. The fiber optic plate may comprise a plurality of scintillating optical fibers bundled together and oriented such that the longitudinal axes of the fibers are pointed towards a radiation source that is to be located across the detector in the radiation therapy system (i.e., the fibers are focused to the radiation source). The fibers may be made of plastic, and/or any material(s) having X-ray linear attenuation coefficients similar to that of water or human tissue. The linear attenuation coefficient of such materials may be about 1 g/cm$^3$ for water and plastics. The fibers may be focused to a radiation source (i.e., their longitudinal axes may be aligned with the rays of a radiation beam produced by the radiation source). The thickness of the fiber optic plate may be from about 1.5 cm to about 20 cm depending on the X-ray energy of the radiation source and the requirement for the detective quantum efficiency (DQE), e.g., about 5 cm, about 3 cm to about 5 cm, about 5 cm to about 10 cm, about 7 cm to about 12 cm, about 10 cm to about 20 cm, etc. The thickness of the fiber optic plate may also be selected such that it may provide sufficient stopping power for detecting 6MV X-rays for imaging. Orienting the fibers in the optic plate such that their longitudinal axes lie along the ray lines of a radiation beam may help to preserve data relating to the directionality of the radiation beam incident upon the fiber optic plate, and/or reduce light scatter between the fibers and which may help to preserve the pixel resolution of an anatomical image.

Figure 1A:
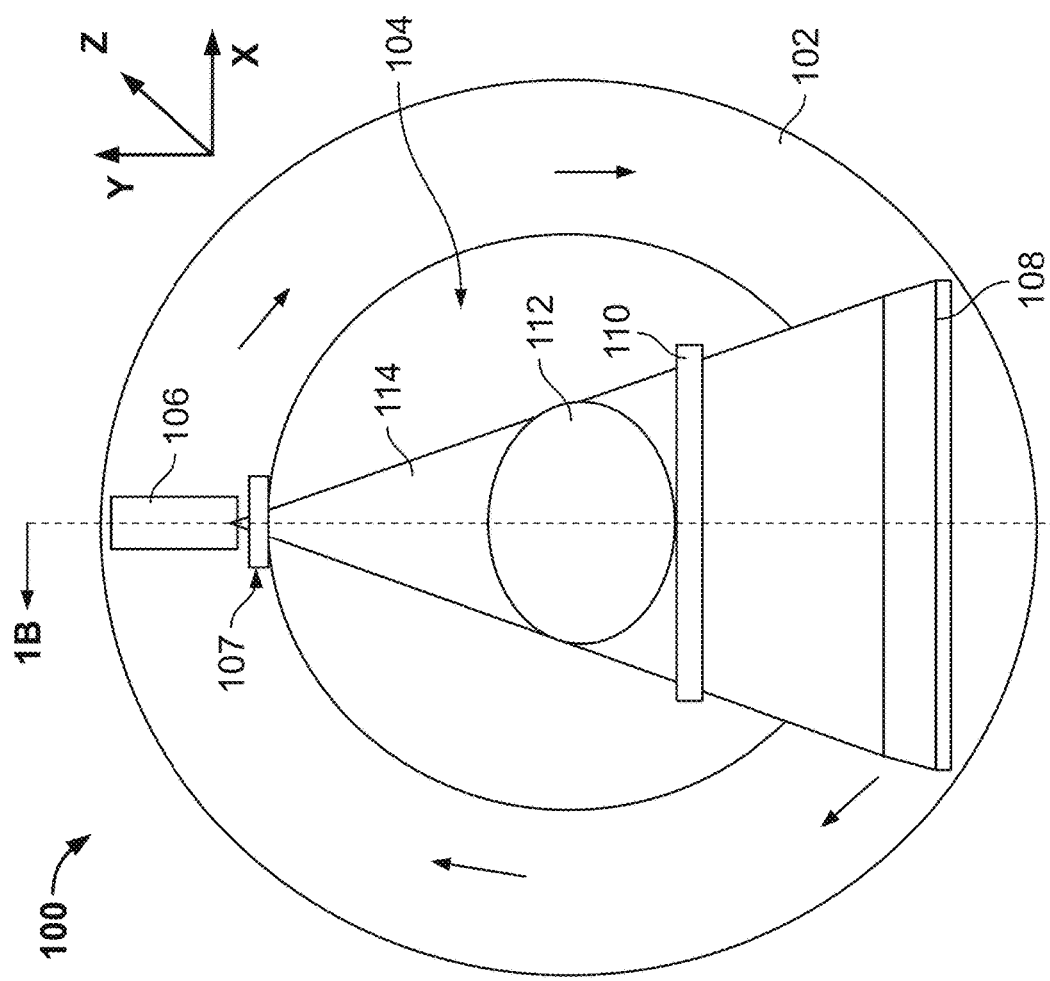
FIG. 1A is an end view schematic depiction of one variation of a radiation therapy system.

FIGS. 1A-B depict one variation of a radiation therapy system. A radiation therapy system 100 may comprise a gantry 102 configured to rotate around a patient area 104, a radiation source 106 coupled to the gantry, a MV detector 108 coupled to the gantry such that it is located across from (i.e., opposite to) the radiation source, and a controller (not shown) in communication with the gantry, radiation source and the MV detector. The gantry 102 may be a rotatable ring or circular gantry and may have a plurality of firing locations at different circumferential locations or angles on the gantry. A collimator 107 may be disposed in front of the radiation source 106 (i.e., within the beam path). A movable patient couch 110 may be located within the patient area 104, and may be configured to move the patient 112 within the patient area, relative to the radiation beam 114 (e.g., fan beam) applied by the radiation source 106. The patient couch may be configured to move the patient in a direction that is orthogonal to a plane of radiation emitted by the radiation source 106, for example, into and out of the patient area 104 which may be defined by the bore or central lumen of the gantry (as depicted by the side view of FIG. 1B). The gantry may be a circular gantry, and may be an open or closed bore gantry, etc. The location of the radiation source 106 may be fixed relative to the location of the MV detector 108. For example, for a particular radiation therapy system or a particular radiation therapy session, the distance between the radiation source and the MV detector, as well as their locations relative to each other, may be determined during and/or before manufacturing, and/or before the therapy session. Maintaining a fixed relative location may allow a MV detector to be tailored to the beam spread of the radiation source (e.g., focused to the radiation source), which may help to reduce the amount of noise detected and/or preserve pixel resolution.

One variation of a MV detector that may be included in a radiotherapy system may comprise a focused scintillating fiber optic plate (FSFOP), a light sensor array such as a photodiode array (e.g., an amorphous silicon (a-Si) photodiode/TFT array) which may be optically coupled to the fiber optic plate, and high frame rate readout electronics in communication with the light sensor array. The fiber optic plate may be an optical device comprising a plurality (e.g., bundle, group, cluster, or block) of micron-sized optical fibers. The optical fibers may scintillate in response to X-ray photons, and may be used both as an X-ray-to-light photon converter and as a light guide to transport light photons to the light sensor array. Generating visible light photons in an optical fiber and transporting those light photons within the same fiber may help to reduce the spread of the light photons along the length of the fibers. Each pixel of the light sensor array may contact and/or receive light photons from a plurality of optical fibers. The fibers in the fiber optic plate may be focused such that they point to the radiation source that is located across from the MV detector in the radiation therapy system.

Figure 1C:
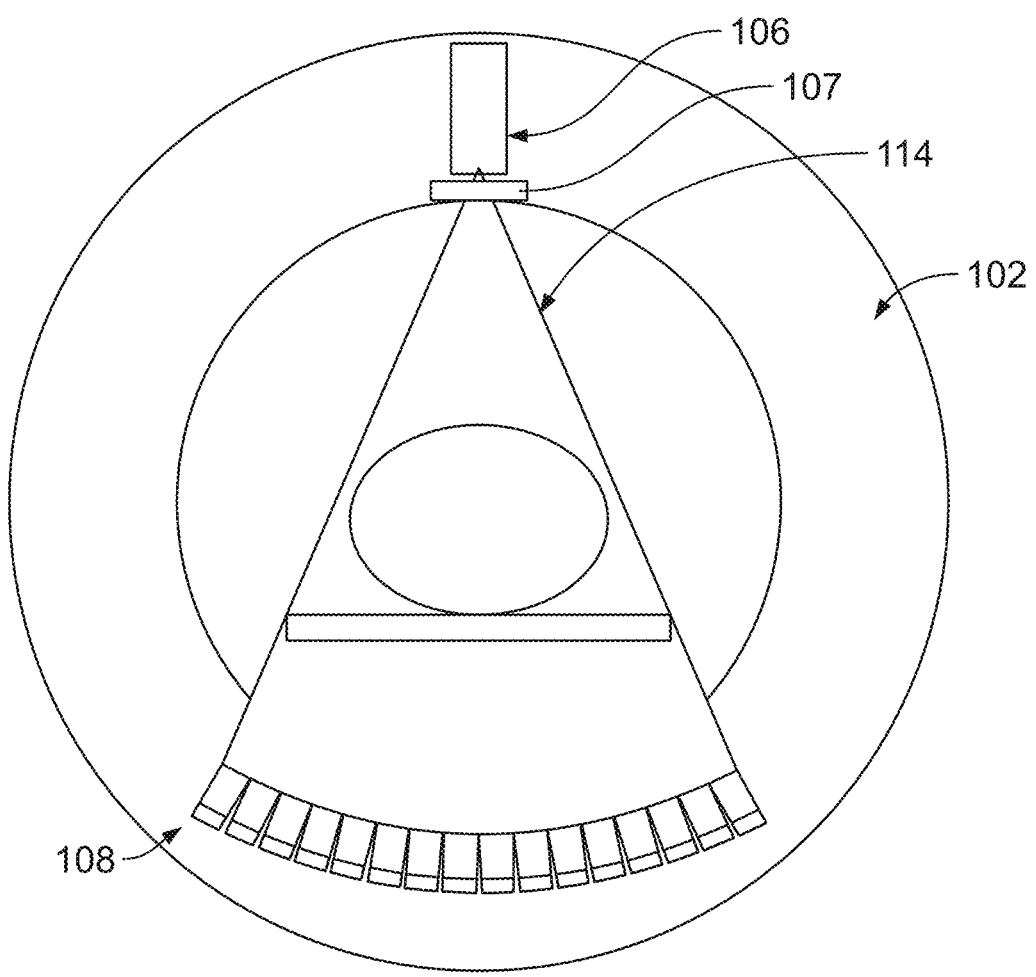
FIG. 1C is an end view schematic depiction of another variation of a radiation therapy system comprising another variation of a MV detector.
Figure 1E:
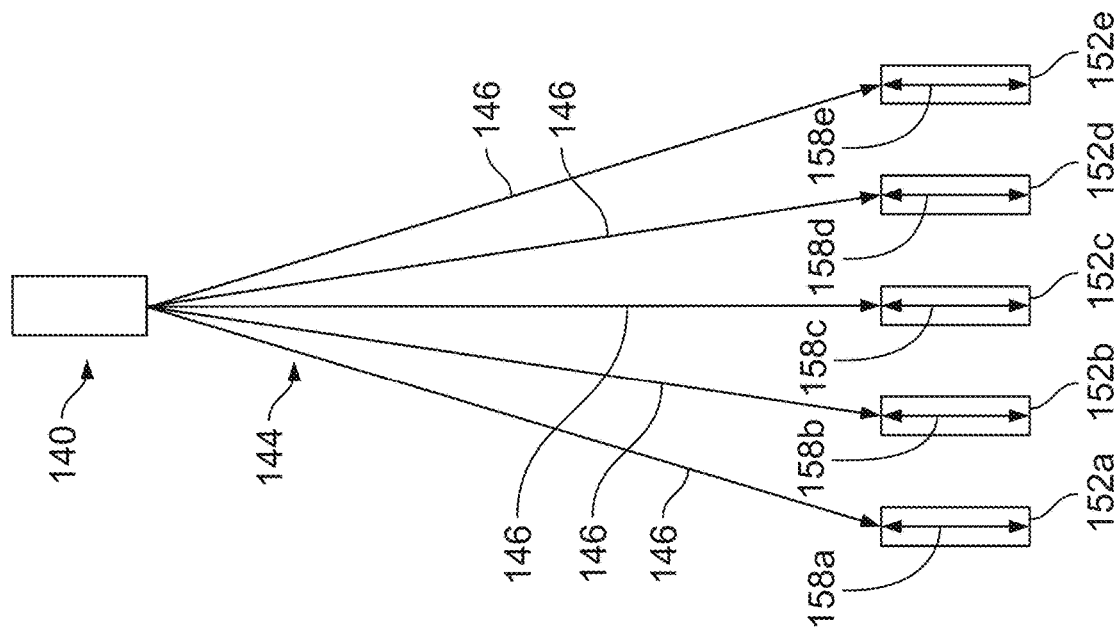
FIG. 1E is a schematic depiction of unfocused fibers.
Figure 1D:
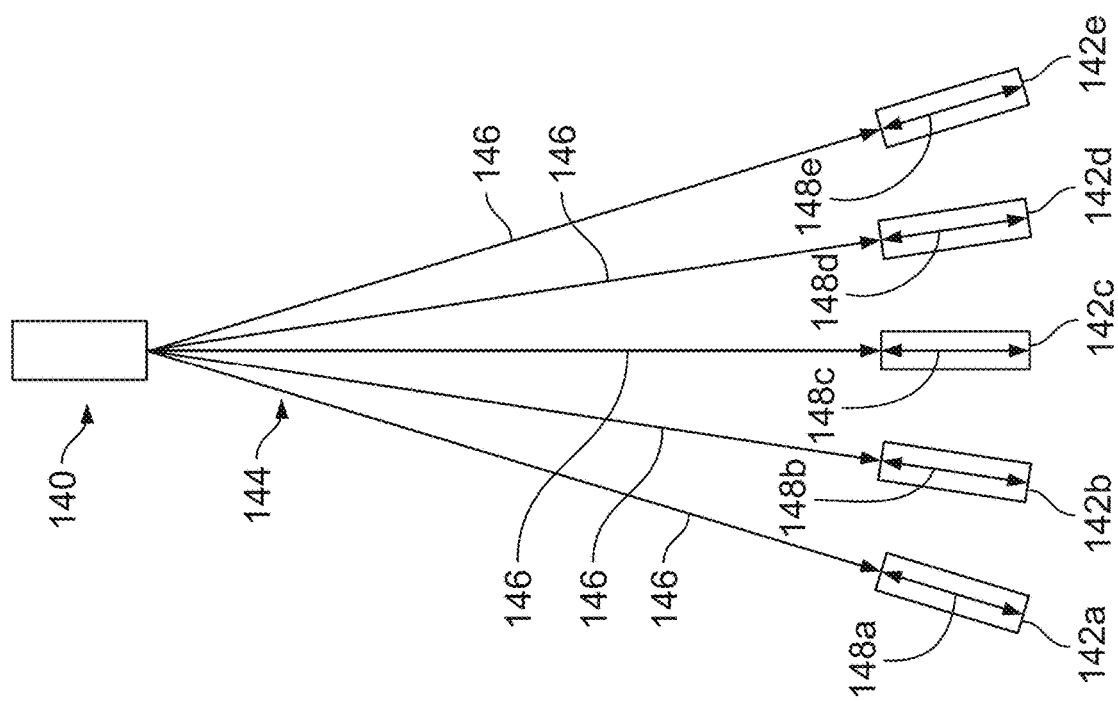
FIG. 1D is a schematic depiction of focused fibers.

As described throughout this document, "focused" optical fibers refer to alignment of the longitudinal axes of the optical fibers to the rays of a radiation beam from a radiation source that is to be located across from the MV detector in a radiation therapy or imaging system. For example, if a radiation source is represented as a focal spot, the radiation beam(s) emanating from it may be represented by a plurality of rays that intersect with and/or originate from that focal spot. The geometry of the radiation beam emanating from the focal spot may be shaped as a cone, a fan, or any other shape as may be determined by one or more radiation beam collimators and/or jaws. An optical fiber may be described as "focused" if its longitudinal axis is approximately or substantially or exactly aligned with a ray of the radiation beam. That is, if the longitudinal axis or length of a focused optical fiber is extrapolated or extended, it would intersect with the focal spot of the radiation source, or nearly or substantially intersect with the focal spot. A cluster, block, or module of optical fibers may be described as "focused" if a majority of the fibers in the cluster, block, or module are aligned with one or more radiation rays (e.g., about 50% to about 100%, about 50%, about 60%, about 70%, about 80%, about 90%, about 75%, etc.). FIG. 1D schematically depicts examples of individual optical fibers 142a, 142b, 142c, 142d, 142e that are focused to a radiation source 140 (note that the fibers are not drawn to scale and may have widths and lengths that differ from the depiction in FIG. 1D). The radiation source 140 may emit a radiation beam 144 that may comprise a plurality of rays 146. The longitudinal axes 148a-148e of each of the fibers 142a-142e may be aligned to a ray 146 of the emitted beam 144. In contrast, FIG. 1E schematically depicts examples of individual optical fibers that are not focused to a radiation source. In FIG. 1E, the longitudinal axes 158a-158e of most of the fibers 152a-152e are not aligned to a ray of the emitted beam. In this variation, the only fiber that may be considered focused is the central fiber 152c that is directly across from the radiation source. Alternatively or additionally, in variations of a MV detector comprising a focused fiber optic plate comprising a plurality of clusters, blocks, or modules, a single cluster, block, or module comprising a plurality of optical fibers may be described as "focused" if the center-most optical fiber of that cluster, block or module is substantially or approximately or exactly aligned with a ray of the radiation beam, and the other fibers in the cluster, block, or module are substantially parallel to the center-most fiber. In the description of a focused fiber optic plate and/or a focused optical fiber, it is understood that the plate and/or fiber is focused to a radiation source, even if a radiation source is not explicitly described or depicted in the description.

While FIGS. 1A and 1B depict a single continuous large rectangular shaped MV detector that spans the full beam width (e.g., the spread or illumination field of the radiation beam at a particular distance from the X-ray or radiation source, the region of irradiation at a particular distance from the radiation source), in other variations, a MV detector may be divided into multiple rectangular or square modules or blocks. For example, as depicted in FIG. 1C, the modules or blocks may be assembled or tiled together to form an overall arc shape that is focused to the X-ray source. In some variations, the MV detectors may be arranged along the curvature of the gantry, i.e., the curve of the arc of modules, may have the same radius of curvature as a circle that is concentric with the gantry. In some variations, the radius of curvature of the overall MV detector may be different from (e.g., greater than or less than) the radius of curvature of the gantry. In some variations, the curvature of the arc shape may correspond to the angular spread of the radiation beam (e.g., fan beam) of the X-ray source. Depending on the requirement for focusing accuracy, individual fibers in the modules may be focused to the X-ray source or clustered into blocks where the fibers are parallel to each other, as described further below.

The overall shape and size of the MV detector may vary as may be desirable according to different X-ray beam geometries, gantry geometries (e.g., size, shape), and/or to fit with the particular arrangement of different radiation treatment systems. For example, a C-arm radiation therapy system may comprise a square-shaped MV detector, while a helical tomotherapy system may comprise a long, rectangular detector. Although the examples of MV detectors described herein are in the context of a helical tomotherapy radiation system, it should be understood that the shape and size of the MV detectors may vary depending on the arrangement of the radiation therapy system desired. The orientation of the fibers in the fiber optic plate may be adjusted in accordance with the relative locations of the MV detector and the radiation source of a particular radiation therapy system such that the optical fibers of the MV detector are focused to the radiation source.

Scintillating fibers (which may be, in some variations, made of plastic) may be bundled together to form a thickened fiber optic plate. As the thickness of the fiber optic plate increases, the X-ray stopping power of the plate may also increase. Scintillating fibers emit visible photons when irradiated by X-rays. The scintillating fibers of the fiber optic plate may be arranged such that they are focused to the radiation source (e.g., to a focal spot of a linac). As described above, the FSFOP may function both as an X-ray-to-optical photon converter and as a light channel to guide the optical photons to the photodiode/TFT array. The optical fibers of the plate have a relatively small diameter as compared to the size of the pixels of the light sensor array (e.g., a photodiode/TFT array). For example, the diameter of a scintillating optical fiber may be from about 1 μm to about 50 μm (e.g., from about 5 μm to about 50 while the width of a pixel may be from about 100 μm to about 1000 μm, e.g., about 100 μm to about 200 μm, about 400 μm. The ratio of the fiber diameter to pixel width may be from about 1:5 to about 1:100, e.g., about 1:10, about 1:15, about 1:20, about 1:30, etc. The small diameter and the light channeling property of the scintillating optical fibers may address the factors that hinder pixel resolution and image clarity. That is, fiber optic plates that have fibers with diameters smaller than the pixel size of a photodiode/TFT array may give rise to images with better resolution than fiber optic plates that have larger diameter fibers (e.g., where the fiber diameter is approximately the same as the pixel size). Fiber optic plates where the fibers have a diameter that is on the same order of magnitude (or substantially similar to) the width/length of a pixel may require that each fiber is aligned with exactly one pixel to facilitate the formation of images with a desirable resolution and sharpness. Fiber misalignment may cause the visible light photons from a single fiber to be randomly fed to two or more pixels, which may contribute to image blur and loss of resolution. However, precise and specific alignment between the fibers of a FSFOP and the pixels of a light sensor array may be challenging due to imprecise positioning of the FSFOP and the light sensor array during the manufacturing process. Misalignment between fibers and pixels may cause cross-talk between neighboring pixels that are receiving light input from the same fiber. In variations where the fibers have a diameter that is approximately the same size as the pixel width of the photodiode/TFT array, such cross-talk may degrade both the spatial resolution and the signal uniformity of the photodiode/TFT array. For example, if the size of a pixel of a photodiode/TFT array is about 400 μm and a fiber has a diameter of the same or similar size, misalignment between the fiber and the pixel by an offset of about 200 μm may cause the light signal from the fiber to be input to two neighboring pixels equally. In this hypothetical scenario, the spatial resolution of the photodiode/TFT array may degrade up to about 800 μm, despite the native pixel resolution being about 400 μm. The degradation to pixel resolution may be reduced by using fibers having a much smaller diameter than the pixel size. For example, where the fiber diameter is about 50 μm and the photodiode/TFT array pixel size is about 400 μm, a single fiber that contacts two neighboring pixels (i.e., providing light input to two adjacent pixels) would result in a light signal spread of no more than about its diameter of 50 μm (instead of about 400 μm in the previous example). This reduced level of cross-talk may help reduce the degradation of spatial resolution of the photodiode/TFT array, and in some variations, limit the level of cross-talk between pixels such that the degradation to spatial resolution is negligible.

Misalignment between fibers and pixels of approximately the same size may cause the septa between the fibers to occupy light-sensitive regions of the photodiode/TFT array. The thickness of septa or cladding in between each of the fibers may result in relatively large and contiguous areas on the sensor pixel where light data may not be sensed (e.g., sensor "dead zones"). Reducing the diameter of the fibers such that they are substantially smaller than the size of a pixel may help to alleviate these issues. Reducing the diameter of the fibers such that they are substantially smaller than the size of a pixel may help to alleviate these issues. Fiber optic plates where the fiber diameters are substantially smaller than the size of a pixel (e.g., where the fiber diameter is at least about 4 times, or about 5 times, or about 8 times, or about 10 times, or about 13 times, or about 15 times, or about 25 times, or about 33 times, or about 50 times, or about 75 times, or about 100 times, etc. smaller than the smallest dimension of a pixel) may not require a one-to-one fiber-to-pixel mapping in order to preserve image quality. Rather, the light output of a plurality of fibers may be mapped to a single pixel. Since the longitudinal axes of a population of fibers may be, as a group, aligned to the rays of a radiation beam emitted by a radiation source (i.e., focused to a radiation source), the average light signal acquired by the photodiode/TFT array from this population may preserve and/or approximate the direction from which the incident X-ray originated. As a result, averaging the signals from multiple fibers across a single pixel may help to smooth out an image. Furthermore, the septa or cladding between each of the smaller-diameter fibers may be distributed across the pixel, instead of in a few contiguous regions, which may help to reduce the size of individual dead zones and average the effect of such dead zones across the area of the pixels. In some variations, averaging signals across multiple pixels may also help to smooth out the image.

Figure 1G:
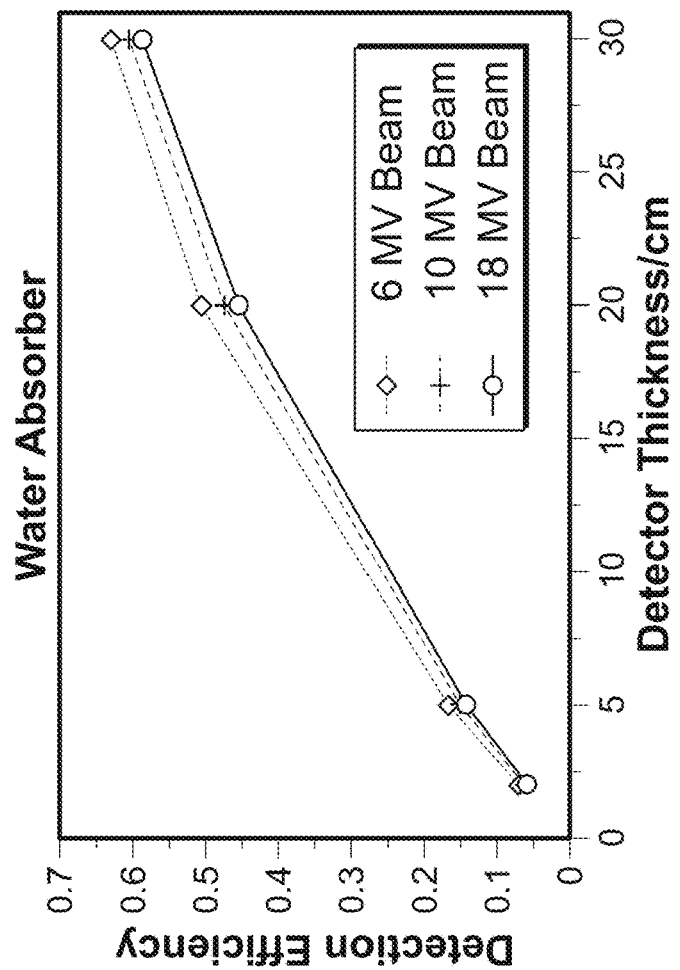
FIG. 1G is a plot of detection efficiency as a function of detector thickness over several radiation source (e.g., X-ray) energies, where the detector comprises a water-like material.
Figure 1F:
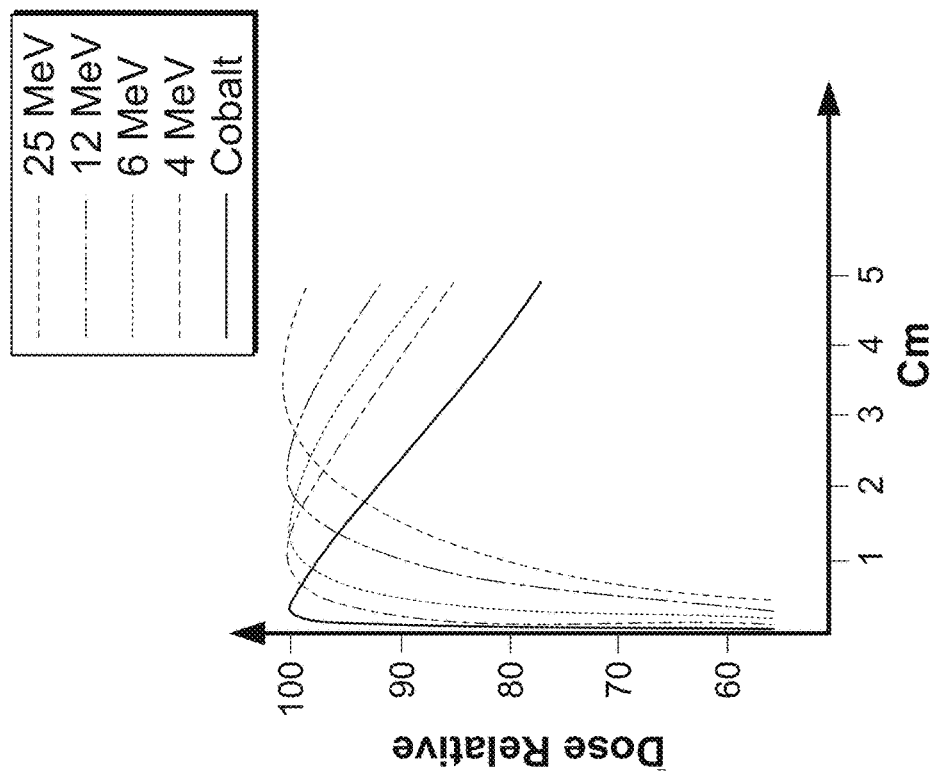
FIG. 1F depicts percentage dose deposition (PDD) curves for a water-like material for different radiation source (e.g., X-ray) energies, including a PDD curve for cobalt for comparison.

The fibers of a fiber optic plate (e.g., a FSFOP) may be made of any material(s) that have mass-energy absorption coefficients and collision stopping powers similar to that of water. For example, the fibers may be made of one or more low-Z, low-density materials, and/or materials with low atomic numbers that are similar to water, and/or any materials with a water-equivalent dose response to radiation. Plastic materials such as polystyrene (e.g., BCF-60), and acrylic may be included in the fibers of the fiber optic plate. Measurement of the amount of radiation delivered to the scintillating optical fibers that have a dose response similar to water may then be used as a model or proxy for the amount of radiation that may be delivered to tissue (e.g., a region of interest in a patient). MV detectors comprising scintillating optical fibers having a dose response similar to water may also allow for calibrations (e.g., dose calibrations) without a water phantom. A dose-depth distribution curve, such as a percentage dose deposition (PDD) curve for a variety of X-ray source energy levels (e.g., 4 MeV, 6 MeV, 12 MeV, 25 MeV) as a function of water depth is depicted in FIG. 1F. For comparison purposes, the PDD curve for cobalt for a 1.25 MeV energy X-ray source is also depicted. For the purposes of this document, the power or energy level of the X-ray radiation emitted by a radiation source will be described as either "MV" (megavolts) or "MeV" (mega electronvolts), where these quantities are related as follows: an electron moving through an electric potential difference of 1 MV gains 1 MeV of energy. The cumulative amount of radiation dose applied to a tissue across a particular depth may be estimated by integrating the dose-depth curve across the length of the fiber (which maps to the thickness of the FOP). The PDD for water is relatively small at superficial skin depths (e.g., at depths less than about 0.5 cm) and increases to peak values at depths of about 1.4 cm for a 4 MeV beam and about 3.5 cm for a 25 MeV beam. As such, the thickness of a FSFOP, or the length of the fibers of a FSFOP, may be from approximately 1.5 cm (or at least about 1.5 cm) to approximately 4 cm (or approximately 5 cm) in order to absorb and/or measure the peak dose delivered by a X-ray source having an energy from about 6 MeV to about 25 MeV (which may provide an estimate of the radiation dose delivered to a patient). A FSFOP thickness (or fiber length) that is shorter than 1.5 cm may not allow the detector to capture the peak dose delivered, may result in a measurement that is a significant underestimate of the amount of radiation that would be delivered to a region of interest in a patient (which is usually more than 1.5 cm beneath the skin surface). Accordingly, an MV detector adapted for dosimetry purposes may comprise an FSFOP where the fiber material(s) have a water-equivalent dose response, as described above, and have a plate thickness (i.e., fiber length) of at least about 1.5 cm in order to capture at least the peak radiation dose. In principle, thickening the FSFOP (i.e., lengthening the fibers) may increase the efficiency of the MV detector, however, increasing the thickness (or length) may introduce other challenges, such as difficulty in aligning the longitudinal axis of a lengthy fiber to the rays of a radiation beam emitted by an X-ray or radiation source, which may result in light spread (e.g., blurring), etc. While the thickness of a FSFOP (e.g., lengths of the fibers) may be longer than about 1.5 cm (e.g., about 2 cm, about 2.5 cm, about 3 cm, about 3.5 cm, about 4 cm, about 4.5 cm, about 5 cm, about 5.5 cm, about 6 cm, about 6.5 cm, about 7 cm, about 7.5 cm, about 8 cm, about 8.5 cm, about 9 cm, about 9.5 cm, about 10 cm, etc.), the desired thickness of the FSFOP may be determined at least in part by one or more of the following: the physical space limitations of the radiation therapy system, desired X-ray stopping power (and therefore amount of X-ray data collected for imaging), image quality, and/or the precision of manufacturing processes. For example, a FSFOP having focused fibers or fiber blocks may be manufactured such that the focus of the fibers to the radiation source and/or alignment of the fibers to rays originating from the radiation source may be within a predetermined tolerance. As the fibers lengthen and the FSFOP thickness increases, the precision of the fiber focus and/or alignment may exceed the predetermined tolerance. Longer fibers may be more difficult to precisely focus than relatively shorter fibers. Unfocused or misaligned fibers may reduce image quality, for example, by increasing blur across multiple fibers and array pixels. The FSFOP thickness and/or fiber length may be selected to balance the need for collecting sufficient data for dosimetry purposes and for imaging purposes. Furthermore, FSFOP that exceed a thickness of about 40 cm may encroach on the patient area.

In some variations, the thickness of a fiber optic plate such as a FSFOP may be selected based on the desired detective quantum efficiency for a certain energy X-ray beam and cost effectiveness. The detective quantum efficiency, DQE(f) is a measure of the combined effects of the signal (related to image contrast) and noise performance of an imaging system, generally expressed as a function of spatial frequency. An ideal imaging system would have 100% DQE at all frequencies. For example, a FSFOP having 5 cm thickness can provide about 9% DQE(0) at zero frequency for a 6 MV X-ray. For comparison, a conventional EPID, which typically uses CsI(Tl) or Gadolinium oxysulfide (GOS) scintillator screens plus a 1 mm copper plate, may have about 1% DQE(0). The detector DQE may continue to improve with increasing fiber plate thickness. For example, at 30 cm fiber plate thickness, the DQE may be 37%. FIG. 1G depicts a plot of detection efficiency (which represented the total absorbed X-ray energy that results in a detectable output signal) as a function of the thickness of a detector comprising a water-like material. Higher levels of detection efficiency may help to facilitate collection of sufficient X-ray data for generating images with higher resolution. FIG. 1G includes detection efficiency curves for X-ray or radiation sources of differing energy levels (e.g., 6 MV, 10 MV, 18 MV). For example, a 5 cm thick plate may have about a 18% detection efficiency in a 6MV X-ray beam (which is significantly higher than the 1-2% detection efficiency of conventional EPIDs that have a copper plate). Increasing the thickness of the fiber optic plate, in combination with the material(s) and/or small diameter of the fibers of the optic plate may promote the conditions that allow a MV detector to function as both a high resolution dynamic imaging detector and as a dosimeter for MV therapy applications. A FSFOP comprising a water-like material and having a thickness of about 5 cm may have a detection efficiency that is suitable for measuring X-ray data for imaging purposes while also being able to measure dose distribution data for a 6 MeV to 25 MeV source.

As described above and in variations throughout this document, the material(s) selected for a FSFOP may have water-like properties in order to measure delivered dose. Other variations of MV detectors may have a FSFOP using fiber material(s) having substantially different properties from water (e.g., one with higher density, high absorption properties, greater X-ray stopping power, etc.) may not be as suitable. Examples of such materials may include glass, BGO, CWO, CsI, GOS and the like. Because the dose-depth distribution curve of these materials may be substantially different from that of tissue or water, measuring the dose distribution in such material(s) may not provide an accurate measurement of dose distribution in tissue. While such fiber material(s) may be suitable for collecting data for generating images (due to a higher X-ray stopping power as compared to water), the precision of the dose distribution measurements acquired by such MV detectors may be compromised or reduced as compared to MV detectors that use fiber material(s) with water-like properties.

Figure 2:
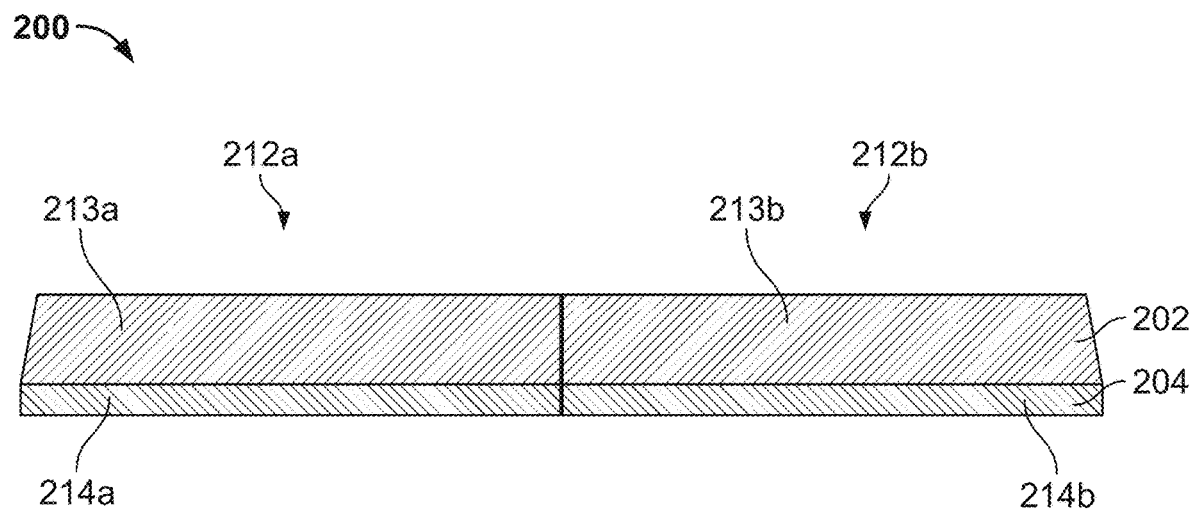
FIG. 2 depicts a cross-sectional view of one variation of a fiber optic plate and flat panel photodiode/TFT array of a MV detector.

FIG. 2 depicts one variation of a MV detector configured to detect radiation for both imaging and dose measurements. The MV detector 200 may comprise a fiber optic plate 202, a photodiode array 204 optically coupled to the fiber optic plate and configured to receive photons from the plate, and data collection/transfer readout electronics in communication with the photodiode array (not shown). For example, the fiber optic plate 202 may be a FSFOP, the photodiode array 204 may be an amorphous silicon (a-Si) array (e.g., active matrix flat panel imager) or a crystal silicon photodiode and thin-film transistor (TFT) array or other photon imaging devices (CCD, CMOS imaging arrays). The MV detector 200 may comprise a left detector module 212a and a right detector module 212b, each of which may comprise a block or cluster of scintillating fibers 213a,b that are focused to a radiation source (e.g., fibers of each block are aligned to different rays of a radiation beam), and separate photodiode arrays 214a,b and separate readout electronics (not shown). The left and right modules 212a,b may be located adjacent to each other to form a rectangular or trapezoidal shape. Although a multi-module MV detector is depicted in FIG. 2, it should be understood that an MV detector may not be sub-divided into multiple modules, and may instead be a single FSFOP unit with a single photodiode array and a single unit of readout electronics. In this example, the thickness of the fiber optic plate 202 may be about 5 cm, and the length of the MV detector 200 may be about 88 cm.

Figure 3:
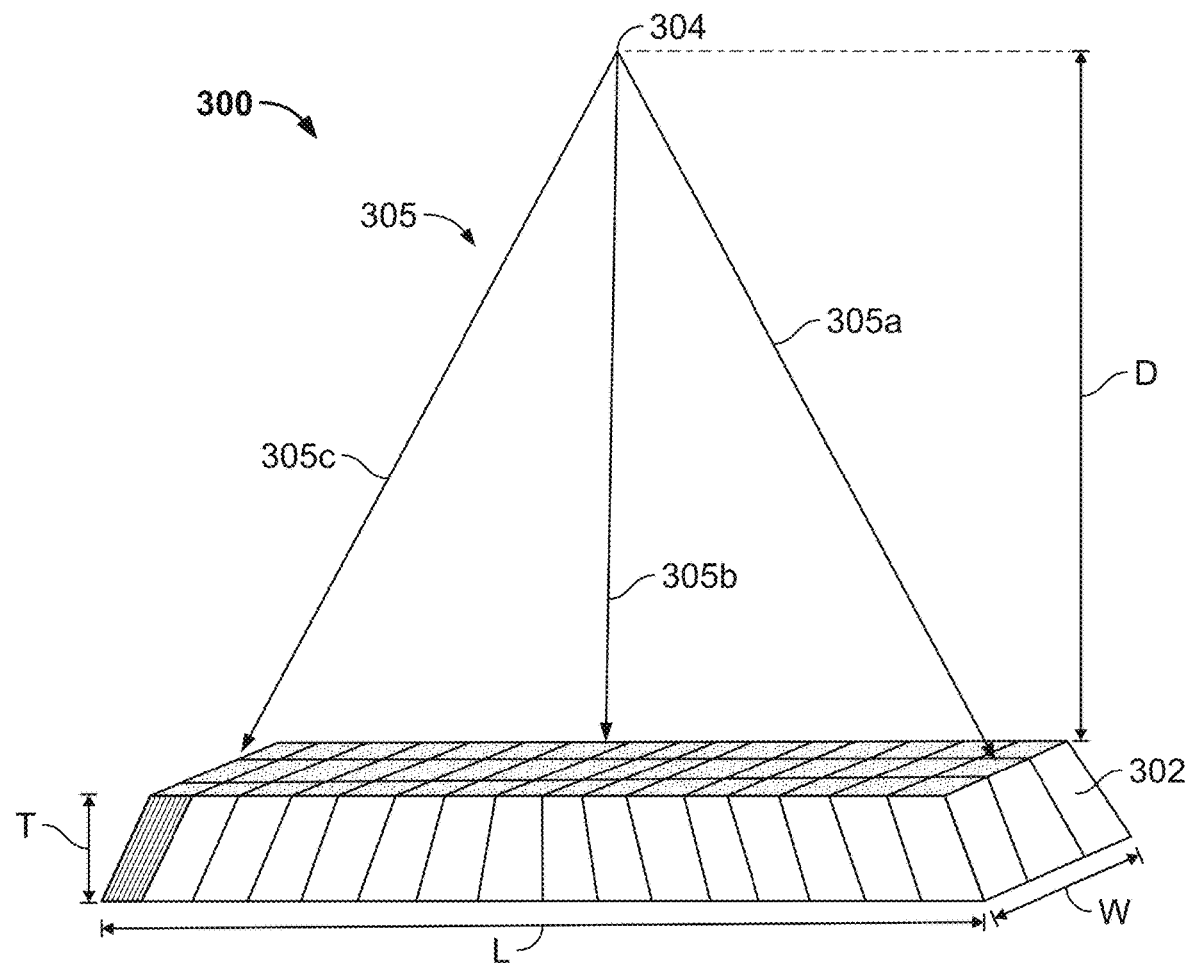
FIG. 3 depicts a perspective view of one variation of a fiber optic plate.

FIG. 3 depicts another variation of a fiber optic plate that comprises an array of fiber optic blocks, where each of the fiber optic blocks is focused to a radiation source. The longitudinal axes of the fibers of a fiber optic block may be aligned to a ray of a radiation beam emitted by the radiation source such that the fiber optic block is focused to the radiation source. In some variations, a fiber optic plate may comprise a first fiber optic block comprising fibers that are slanted at a first angle with respect to a top face (e.g., light input face) of the fiber optic plate such that their longitudinal axes are aligned with a first ray of the radiation source, and a second fiber optic block comprising fibers that are slanted at a second angle with respect to a top face of the fiber optic plate such that their longitudinal axes are aligned with a second ray of the radiation source. The first angle and the second angle may be different, due to the different locations of the first fiber optic block and the second fiber optic blocks on the fiber optic plate. The fiber optic plate 300 may comprise a plurality of fiber optic blocks 302 that together form a plate having an overall trapezoidal shape. In the variation of a fiber optic plate of FIG. 3, the fiber optic plate 300 comprises 48 (3×16) blocks of focused scintillating optical fibers, where each of the 16 blocks are focused to different or unique rays 305a, 305b, 305c of a radiation beam 305 emitted from the radiation source 304. Although the fiber optic plate 300 is depicted as having fiber optic blocks 302 that are focused to the radiation source (which may be represented by a focal spot) 304 in two dimensions (e.g., along the x and z directions), it should be understood that the fiber optic blocks 302 may be focused to the radiation source 304 in three dimensions (e.g., along the x, y and z directions). The radiation source may be any distance above the plate, and the patient area may be located in the space between the radiation source 304 and the fiber optic plate 300. For example, the distance D between the radiation source and the MV detector (e.g., the fiber optic plate) may be from about 110 cm to about 150 cm, e.g., about 132.5 cm. As an example, fiber optic plate 300 may have a thickness T of about 5 cm thick, a length L of about 88 cm, and a width W of about 8 cm.

The individual optic fibers and/or fiber optic blocks of a fiber optic plate may be directly coupled to (e.g., contacting) each other, without any intermediary light-shielding between the fibers and/or the blocks. Optionally, the fiber optic plate may comprise light-shielding layers or septa or cladding between individual fibers and/or between the fiber optic blocks. The light-shielding layer or coating may help to reduce the scatter of X-rays and/or visible light photons from one block and/or fiber to another adjacent block and/or fiber. In some variations, a light-shielding layer that is interposed between blocks and/or fibers may comprise thin sheets of high-Z metals, for example, 0.1 mm thick tungsten or lead. The thickness of the septa or cladding (e.g., the distance between each block) can be made smaller or larger to trade-off between scatter effectiveness and the loss of incoming primary X-rays due to the space occupied by the septa or cladding. For example, the thickness of the septa or cladding may be selected such that the noise arising from inter-fiber scatter and the image blur due to the loss of primary X-rays are able to be corrected using image processing methods. In some variations, a fiber optic plate may comprise any light-shielding layers or septa or cladding between the individual fibers and/or between the fiber optic blocks. The scatter of X-ray and/or visible light photons between fibers may be reduced or blocks by using fibers or waveguides made of materials having different refractive indices and arranging them in an alternating or randomized fashion in the plate so that fibers with different refractive indices are adjacent to each other (e.g., a Tranloc waveguide). The interface between two materials having different refractive indices tends to cause light to reflect at the interface, instead of being transmitted through from one material to the other. By arranging fibers having different refractive indices adjacent to each other, light in one fiber is kept from crossing over to an adjacent fiber. In such matter, the interface between two fibers with different refractive indices may act as a light barrier and may help to reduce light scatter between fibers. In one variation, a fiber optic plate (e.g., FSFOP) may be comprise fibers made of a first material with a first refractive index (e.g., polystyrene) and fibers made of a second material with a second refractive index (e.g., acrylic or poly methyl methacrylate). The fiber optic plate may be made by drawing these two fiber types together such that the fibers are arranged in an alternating or semi-randomized or randomized fashion. A fiber optic plate comprising fibers or waveguides made of two or more materials with different refractive indices (e.g., a Transloc waveguide) may reduce or eliminate the use of cladding or septa between the fibers or blocks, which may reduce the amount of "dead space" occupied by cladding or septa on the surface of the light sensor array.

Other components may optionally be included in a fiber optic plate to help reduce the incidence of scattered X-rays on the photodiode array and/or shield the MV detector from external noise sources, such as from the linac, 60 Hz noise from power supplies, and the like. For example, a MV detector may comprise a fiber optic plate and a cover located on the top surface of the fiber optic plate (i.e., the surface of the MV detector that is closest to the radiation source). The cover may be a thin metal plate made of low-Z metal, for example, 0.2 mm Cu or 1 mm Al. The cover may be electrically grounded, and may be configured to block more scattered X-rays than primary X-rays. Alternatively or additionally, a reflective paint material or coating may be applied between the individual fibers and/or between blocks, which may help to reflect scintillation photons back into the fibers and toward the photodiode array. Alternatively or additionally, a reflective paint material may be applied on the fiber plate surface opposite to the photodiode/TFT array to reflect the light photons towards the photodiode/TFT array.

Figure 4:
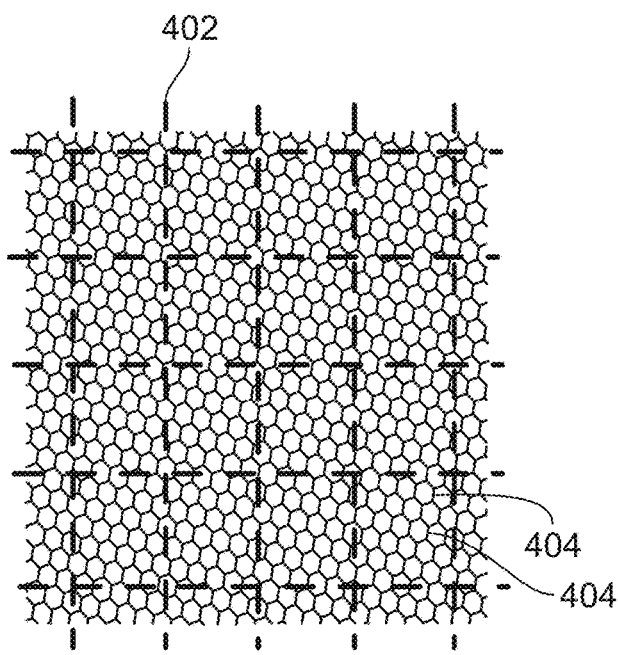
FIG. 4 is a representation of the mapping between the fibers of one variation of a fiber optic plate and the pixel boundaries of a photodiode/TFT array.

As described above, the fiber optic plate may contact and interface with the light sensor array (e.g., photodiode/TFT array) such that visible light channeled through the fibers (or in some variations, generated by the fibers themselves) impinges on the light sensor array, which converts the photon incidence to an electrical signal. In some variations, as described above, the fibers of the fiber optic plate may be much smaller than the pixels of the photodiode/TFT array such that multiple fibers map onto (e.g., contact) a single pixel. FIG. 4 depicts one example of how a fiber optic plate may map onto a photodiode array. The thickened dotted lines 402 represent the pixel boundaries on a photodiode array. The boundaries of the individual fibers of the fiber optic plate (e.g., a plastic scintillator array) are represented by the thin lines 404. The fibers 404 have a much smaller diameter than the pixel width of the photodiode/TFT array (e.g., where the ratio between the fiber diameter to the pixel width is about 1:20). Instead of a one-to-one mapping between the fibers and the pixels (i.e., the fibers of a fiber optic plate and the pixel boundaries of a photodiode array are not aligned such that one each pixel is in contact with exactly one fiber), multiple fibers map onto a single pixel and the uniformity of each pixel may be achieved by the averaging effect. That is, light signals from multiple fibers impinging on a single photodiode/TFT pixel may be summed and averaged by that photodiode/TFT. In this example, the diameter of the fibers may be from about 5 μm to about 50 μm (e.g., about 5 μm to about 10 μm, about 10 μm), while the photodiode array pitch or pixel width may be from about 150 μm to about 600 μm (e.g., about 400 μm). In some variations, a single pixel may be in contact with and/or receive light data from anywhere between 10 to 200 fibers, e.g., 10, 20, 25, 30, 50, 100, 10-100, 50-200, etc., fibers. The fiber optic plate may be coupled to the light sensor array such that there is little, if any, air at the plate-array interface. For example, one or more clamps around the perimeter edge of the fiber optic plate may be used to secure the fiber optic plate to the light sensor array. Optionally, the surfaces of the fiber optic plate and the light sensor array that contact each other may be polished to help facilitate an air-free interface between the fiber optic plate and sensor array. Alternatively or additionally, adhesives may be provided between the fiber optic plate and the light sensor array (e.g., around the perimeter) to secure these components together.

Figure 5:
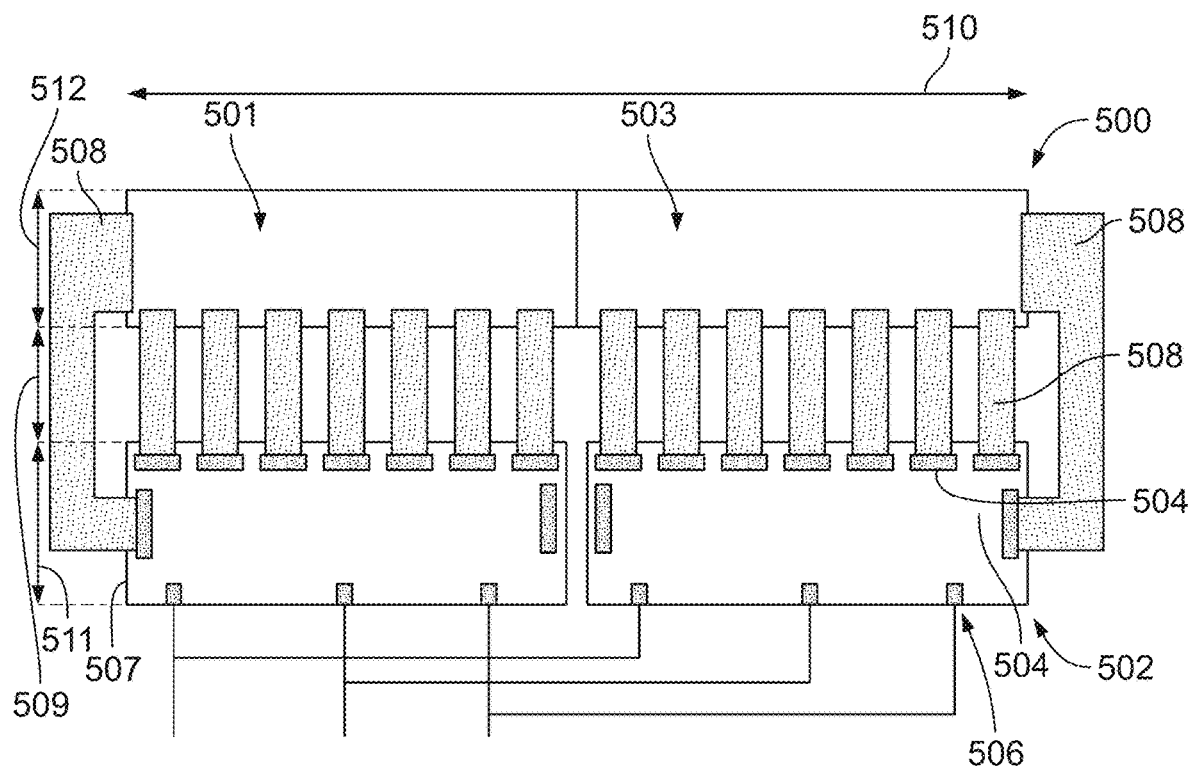
FIG. 5 is a schematic representation of one variation of photodiode array and the readout electronics.

The light data collected by the photodiode/TFT array (which may be an a-Si detector) may be in communication with readout electronic circuitry, which are schematically depicted in FIG. 5. In some variations, an a-Si photodiode/TFT array or a-Si detector 500 may be in communication with electronic circuitry 502 configured for dynamic high-frame-rate readout. The a-Si detector 500 may comprise a first diode array 501 (e.g., left diode array) and a second diode array 503 (e.g., right diode array). The readout electronic circuitry 502 may comprise one or more PCB or electronic substrates 507, and a plurality of data connectors 504 configured to capture a dose distribution image for each linac beam pulse (which may be about 100-200 frames per second) and to transmit detector data to electronic components (e.g., machine-readable memories, multiplexors, microprocessors, and the like) that may be mounted on the substrate 507. In one variation, readout electronic circuitry may comprise additional connectors 506 for power and/or control signals. Connectors 506 may include connectors for signals that contain timing synchronization data (e.g., trigger signals), connectors for network interface and data exchange (e.g., Ethernet connections, GigE-capable connections), and/or connectors for power. The system controller and/or linac may provide a sync signal to the readout electronic circuitry to coordinate the timing between the application of the radiation beam and the acquisition of light data from the MV detector. The interconnect between the a-Si photodiode/TFT array 500 and the readout electronic circuitry 502 may comprise a flexible wired bus or ribbon or tape 508 having conducting traces (e.g., copper, gold, etc.) embedded in an insulating material, which may be bonded to the detector array and/or connectors using solder or adhesives (e.g., anisotropic conductive adhesives such as anisotropic conductive film or paste). In some variations, the length 509 of the bus 508 between the diode array 501 and the substrate 507 may be about 4 cm and the width 511 of the substrate 507 may be about 10 cm. The a-Si photodiode/TFT array may have a native pixel resolution of about 100 μm to about 200 μm, and may have an overall length 510 of about 85 cm, e.g., about 86.73 cm and a width 512 of about 10 cm. The pixels may be binned to 2×2, 3×3 or 4×4 matrices during the readout to speed up the frame rate and to reduce the image data size. In some variations, the whole photodiode array may consist of a matrix of 4400×400 pixels at the pixel pitch of 0.2 mm During or after the readout, the pixels can be binned in various formats. For example, with a 2×2 binning format, the resulting new matrix would have 2200×200 pixels at pixel pitch of 0.4 mm Binning the pixels may result in proportionally larger effective pixel pitch, or lower resolution.

Figure 6:
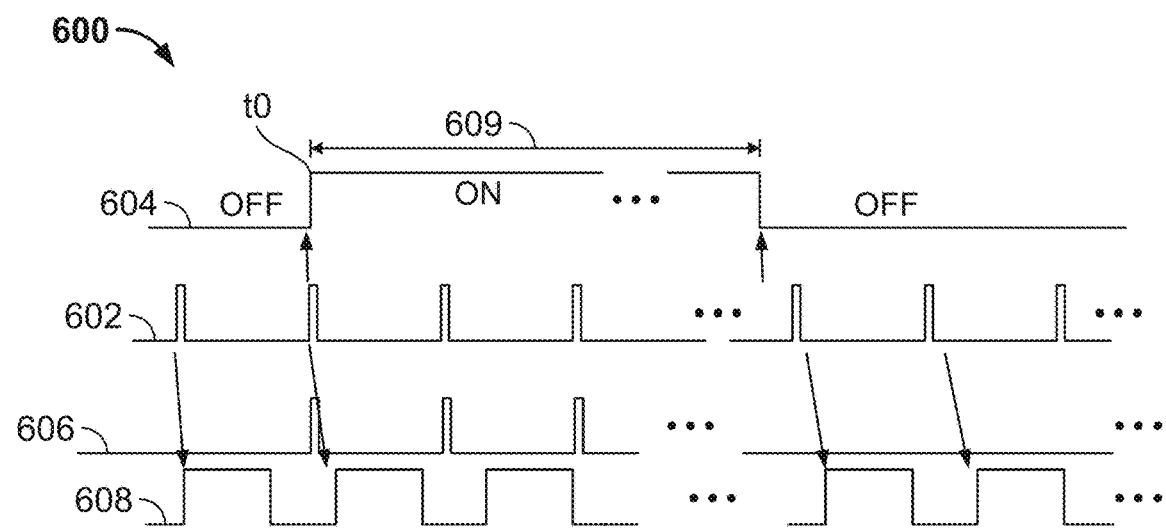
FIG. 6 is a timing diagram of one variation of a treatment image sequencing method.

The controller (e.g., the radiation therapy system controller) may provide control/sync signals to the X-ray source (e.g., linac) and MV detector to synchronize the operation of these components. The control signals may also indicate the mode of operation of the system, and the acquired image data may be sorted, stored, and processed in accordance with the operating mode. One example of a MV detector and linac timing diagram 600 is illustrated in FIG. 6. As depicted there, a linac modulator trigger signal 602 may be generated by the radiation therapy system controller, which may be transmitted to the linac and the MV detector so that the radiation data collection is synchronized with the radiation beam firing event. In this variation, the linac modulator trigger signal 602 is a constant periodic signal that triggers the MV detector to acquire an image at a set time interval, regardless of whether the linac has fired a radiation beam or not, but in other variations, the trigger signal 602 may not be synchronous or periodic. The read sync signal 608 synchronizes the data output from the photodiode/TFT array with the data connectors 504. In some variations, the read sync signal 608 may be activated in accordance with the trigger signal 602 (e.g., after a delay), and may represent the transfer of image data from the detector to the controller, which may be offset by a delay after the trigger signal. Image data may be raw data from the photodiode/TFT array, or may be the average of several acquired images (one averaging method is described below and depicted in FIGS. 12A-12B). When the controller transitions to the treatment mode from the non-treatment mode (as indicated by the treatment signal 604 transitioning from a low value to a high value, at time point t0, for example), the controller may send a linac beam pulse 606 to the linac to fire a radiation beam (e.g., X-ray). In this variation, as long as the treatment signal 604 has a high value (indicating that the system is in the treatment mode), the linac beam pulse 606 will pulse according to the trigger signal 602. While the controller is in treatment mode (as indicated by duration 609), the MV detector acquires data that may be used to generate an image or plot of the radiation deposited in the patient. When the controller is not in treatment mode, the data collected by the MV detector may be used to generate "dark" or "offset" images. Dark or offset images may be used to correct background or noise artifacts. For example, the data and/or images acquired in the absence of a linac radiation beam may be subtracted out from the data and/or images acquired in the presence of a linac radiation beam to compensate for the effects of detector dark current.

Figure 7A:
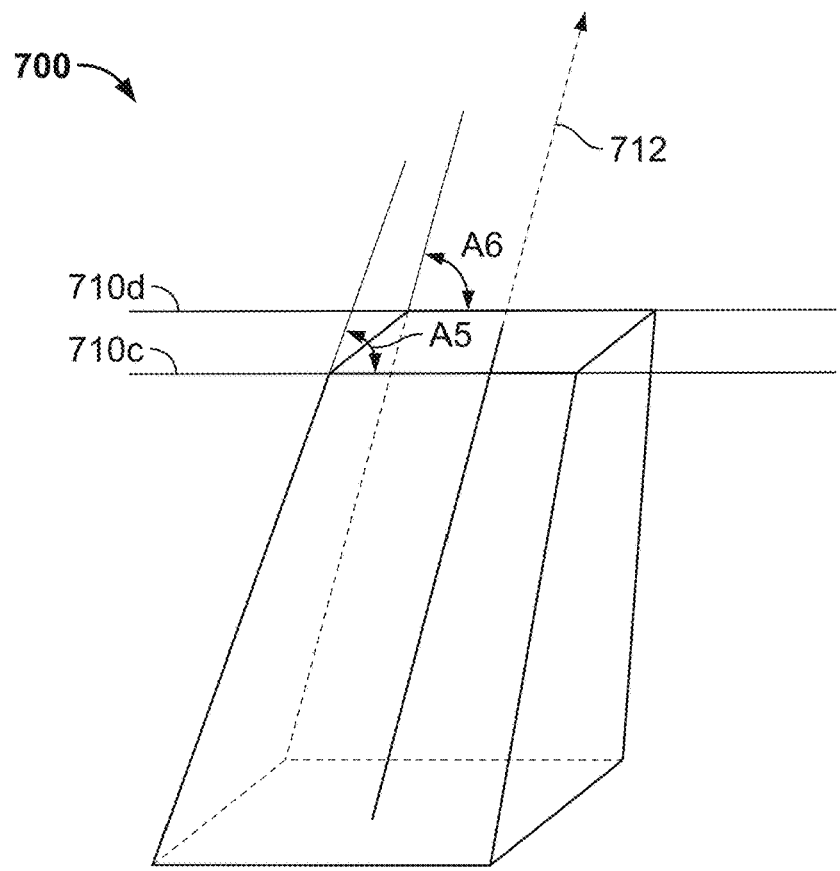
FIG. 7A is a perspective view of one fiber optic block of a fiber optic plate of a MV detector.
Figure 7B:
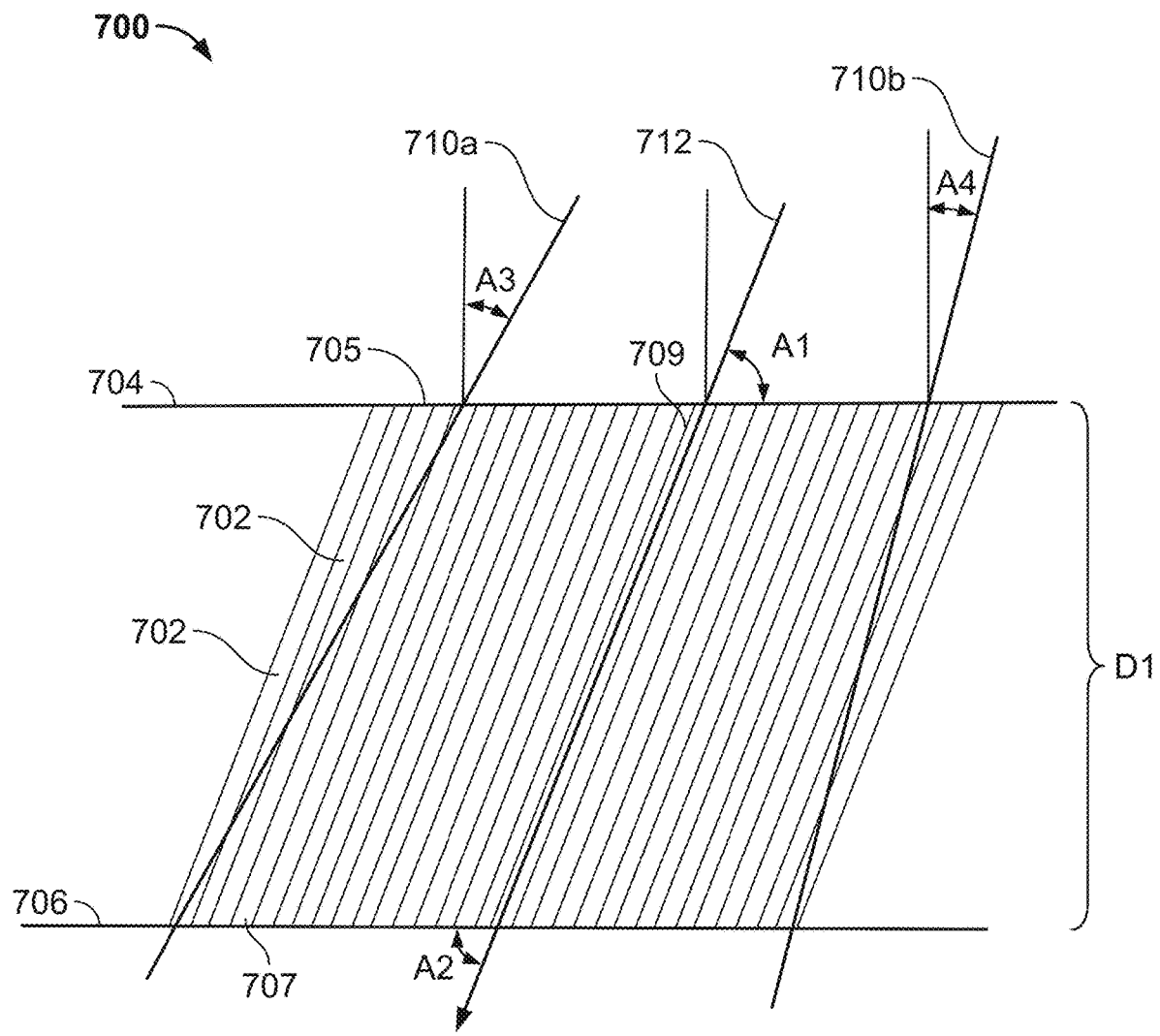
FIG. 7B is a side schematic view of one fiber optic block made in accordance with the method outlined in the flowchart of FIG. 7C.
Figure 7C:
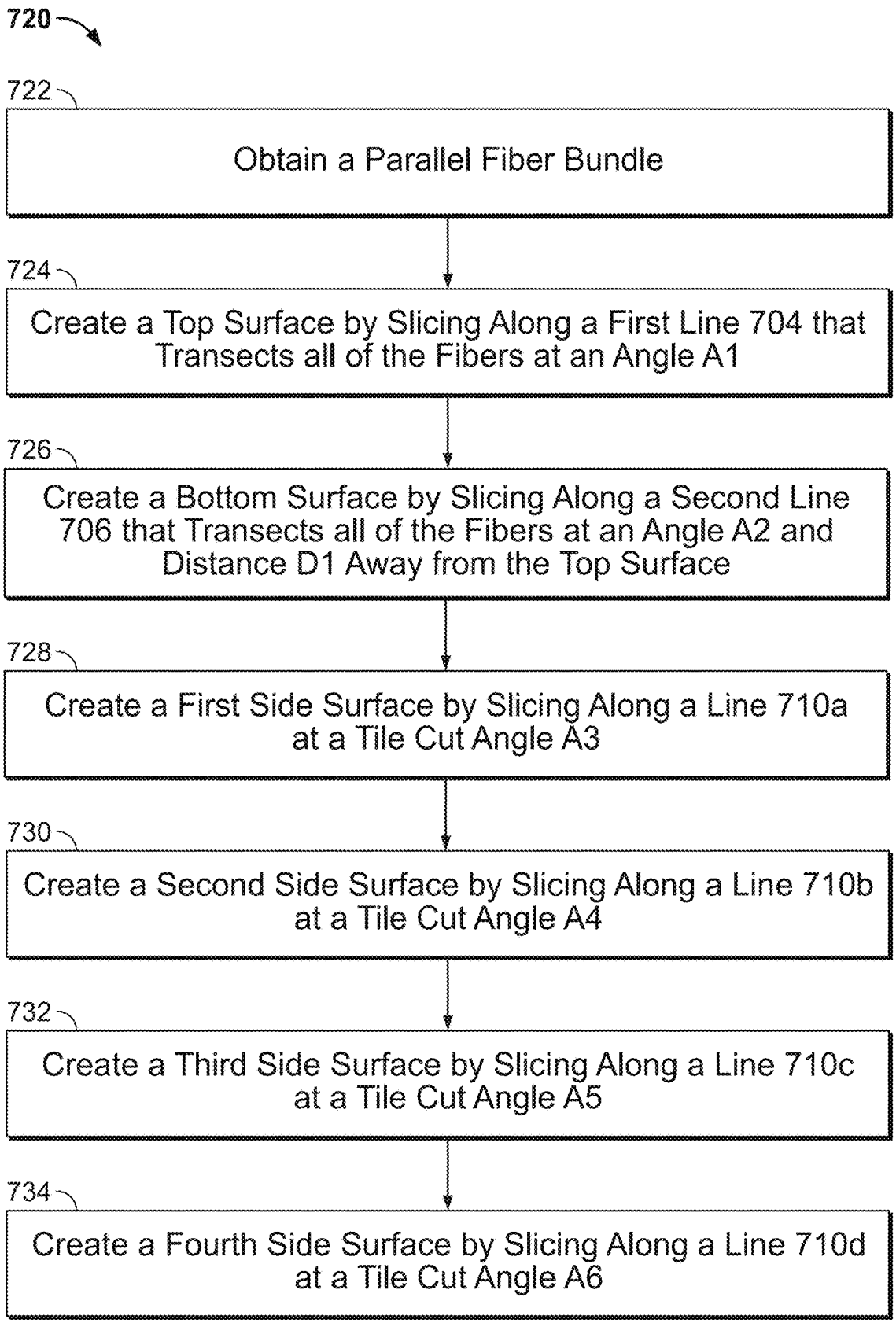

Described herein are methods of manufacturing fiber optic plates for a MV detector that may be used for both anatomical imaging and radiation dose measurements. As described above, a fiber optic plate may comprise a plurality (e.g., an array) of optical fiber blocks or bundles coupled together. The individual blocks may be manufactured separately and then assembled together to form a complete optical fiber plate. For example, a FSFOP may comprise a plurality of scintillating fiber optic blocks, where each block comprises fibers having longitudinal axes that are aligned to a ray of a radiation beam emanating from a radiation source. Different blocks may comprise fibers with longitudinal axes that are aligned to different rays of the radiation beam, such that each of the blocks is focused to the radiation source. The size and shape of the FSFOP may vary to correspond with the size and shape of the radiation beam and/or the physical arrangement of a radiation therapy or imaging system. Accordingly, the number and size of the fiber optic blocks may also vary, and each block may have a width from about 1 cm to about 10 cm. Additionally, the angle of the fibers in a fiber optic block may vary depending on the radiation ray to which the block is focused and the location of the block in the overall fiber optic plate. In some variations, at least one fiber in a fiber optic block 700, e.g., the longitudinal axis of the central fiber as depicted in FIG. 7A, is focused to the X-ray source. One method of manufacturing a fiber optic block 700 that has at least one focused fiber, such as the block depicted in FIG. 7A, is depicted in FIGS. 7B-7C. Each block of a fiber optic plate may be individually cut from a plate of parallel fibers at a different specific tilt angles such that the central fibers of each of the blocks are focused. The tilt angle at which each of the blocks are cut may depend on the location of the particular block in the fiber optic plate of the detector assembly. In some variations, only the fiber(s) located near or at the center of the block are focused. The fibers that are further from the center of the block become less and less focused (e.g., deviate more and more from the rays of a radiation source) to the radiation source. In one variation of a method 720 for manufacturing a block or module of fiber optic plate comprising a plurality of blocks or modules, a grouping or bundle of fibers that are substantially parallel may be manufactured or procured 722, according to known methods. The fiber tilt angle (e.g., the angle of the fibers in the block with respect to the line that is normal to the top and bottom surfaces of the block) of each of the fibers in the block may be determined at least in part based on the radiation ray to which the block is to be focused and/or the intended location of the block in the fiber optic plate, and may, for example, be from about 0 degrees to about 90 degrees, e.g., about 0 to about 60 degrees. The method 720 may comprise creating 724 a top surface 705 by slicing along a first line 704 that transects across the fibers at an angle A1 (e.g., the tile face cut angle), creating 726 a bottom surface 707 by slicing along a second line 706 that transects across the fibers at an angle A2 and is parallel to the top surface 705 (i.e., angles A1 and A2 are substantially the same). The second line 706 may be a distance D1 away from the top surface 705. The method 720 may also comprise creating 728 a first side surface by slicing along a line 710a, which is at a tile cut angle A3 (which is the angle from a line that is normal to the top surface of the block), creating 730 a second side surface by slicing along a line 710b, which is at a tile cut angle A4, creating 732 a third side surface by slicing along a line 710c which transects the top and bottom surfaces at a tile cut angle A5, and creating 734 a fourth side surface by slicing along a line 710d which transects the top and bottom surfaces at a tile cut angle A6 (see FIG. 7A). The tilt cut angles A3-A6 may vary for each of the side surfaces, depending on the location of the particular optical fiber block within the entire fiber optic plate, and the overall shape (e.g., trapezoidal or cuboid shape) of the fiber optic plate. These steps may be repeated for each block of the plurality of blocks of the fiber optic plate, but the tile cut angles and tilt cut angles may vary for each of the blocks. In the example depicted in FIG. 7A, at least the longitudinal axis of central fiber 709 is aligned to radiation ray 712, while the longitudinal axes of the fibers adjacent to the central fiber 709 may not be exactly aligned to ray 712. The number or proportion of fibers in a particular block of a fiber optic plate may vary, and may be selected such that the spatial distortions of the resultant images are in the sub-millimeter range (e.g., no more than about 1 mm). In some variations, all (about 100%) of the fibers may be focused, while in other variations, the ratio of focused fibers to unfocused fibers in a block may range from all the fibers being focused, to most of the fibers being focused (e.g., from about 100:1 to about 2:1), to about half of the fibers being focused (e.g., about 1:1). The focused fibers may be distributed across the block, or may be concentrated in the central portion of the block.

Figure 8A:
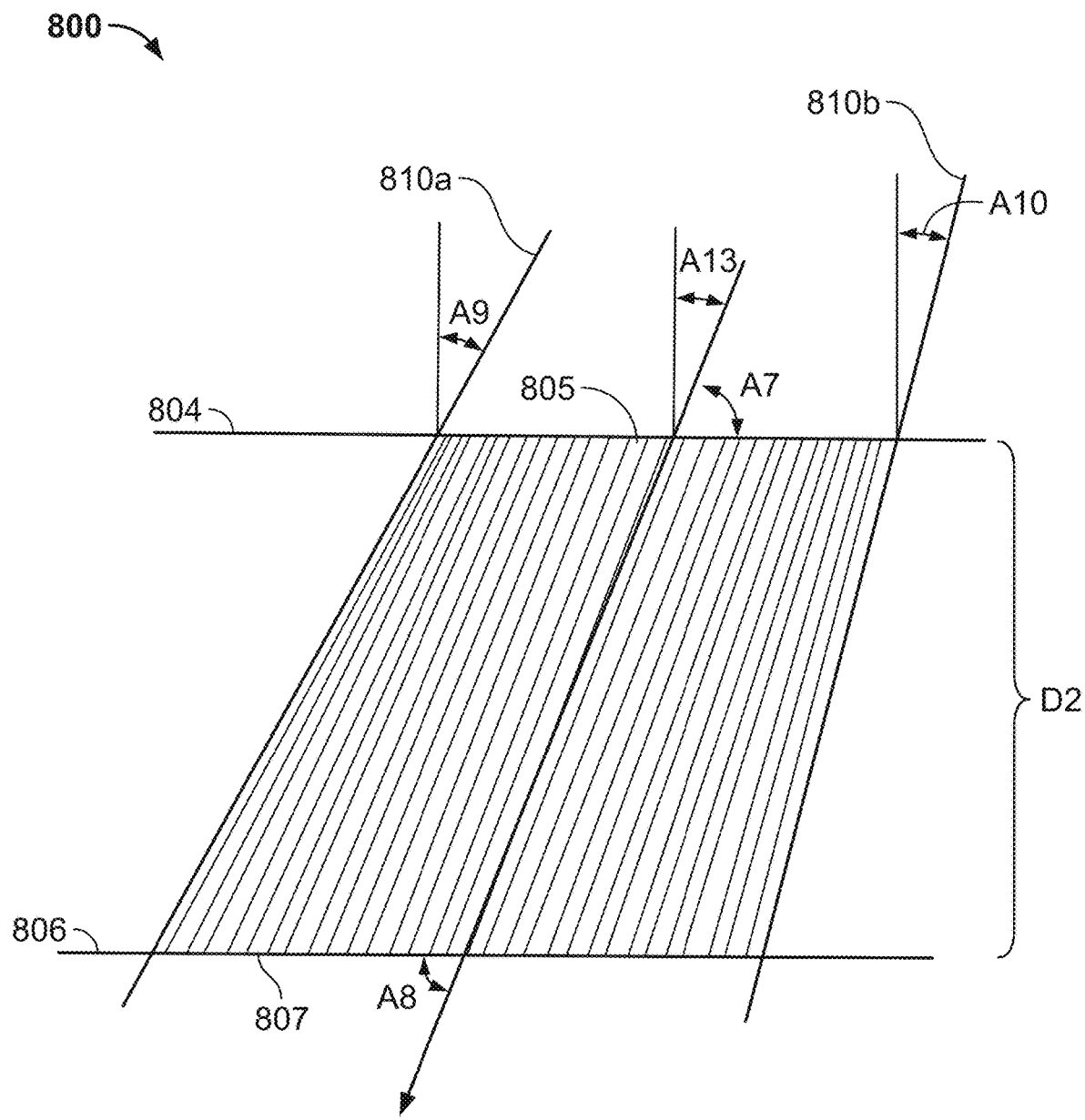
FIG. 8A is a side schematic view of one fiber optic block made in accordance with the method outlined in the flowchart of FIG. 8B.
Figure 8B:
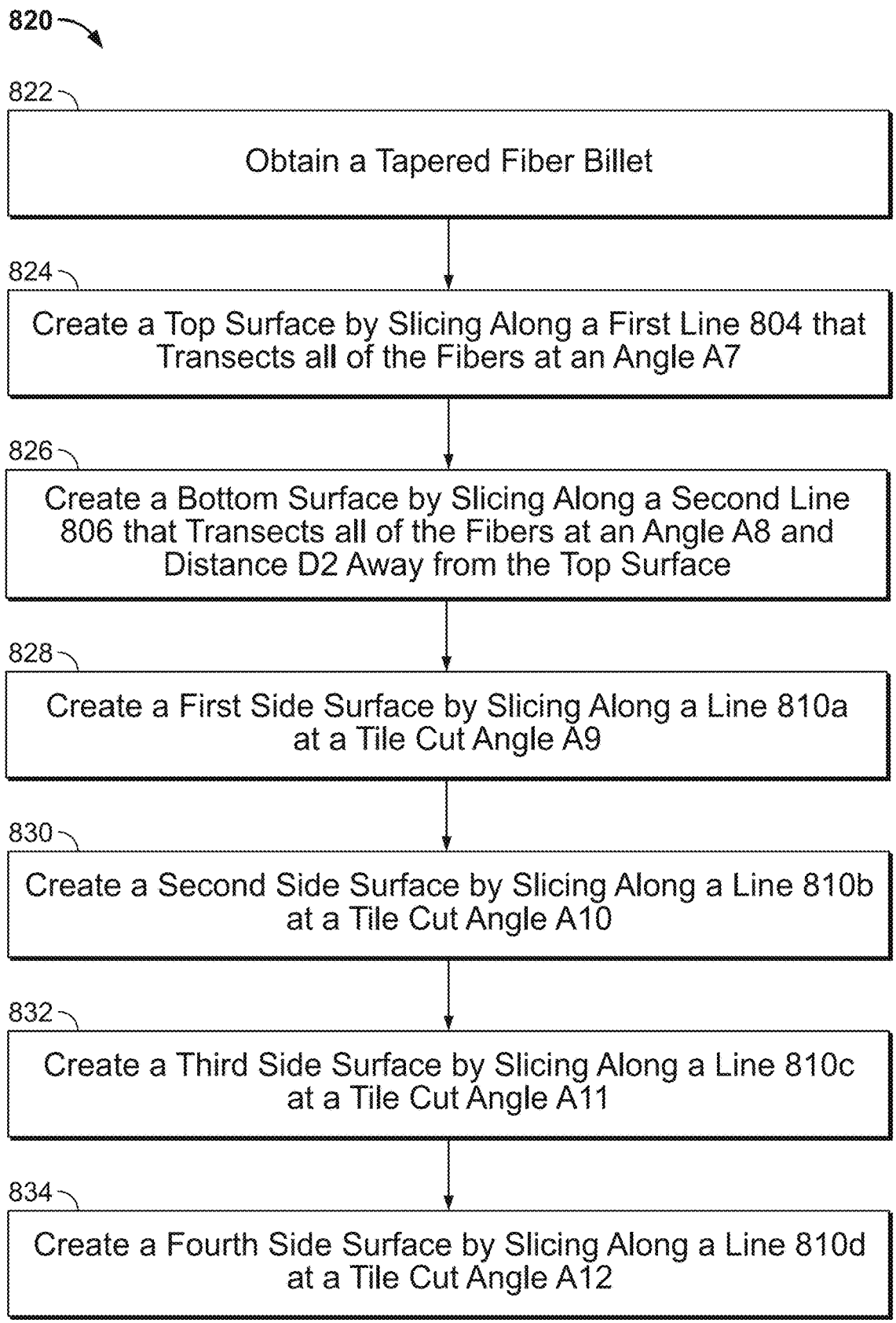
FIG. 8C depicts the coordinates for the computation of fiber tilt angles.
FIG. 8D is a perspective view of the fiber optic block of FIG. 8A.

In some variations, a fiber optic plate may comprise a plurality of fiber blocks, where most, if not all, of the fibers in each of the blocks is focused to a radiation source (e.g., where the longitudinal axis of each fiber is aligned along a ray of the radiation beam). For example, all of the fibers in a block may be focused (e.g., 100% of the fibers) or the proportion of focused fibers to unfocused fibers may be from about 100:1 to about 2:1 (e.g., about 99% to about 51% of the fibers are focused). Such blocks may be considered "fully focused" blocks, since most or all of the fibers are focused to the radiation source. FIGS. 8A and 8B depict one variation of a method 820 for manufacturing a fully focused fiber optic block 800. The method 820 may comprise procuring or manufacturing a tapered fiber billet. The fiber billet may be thermally tapered, for example. The geometry for tapering follows the focal distance and location of the each fiber in the fiber block.

Figure 8C:
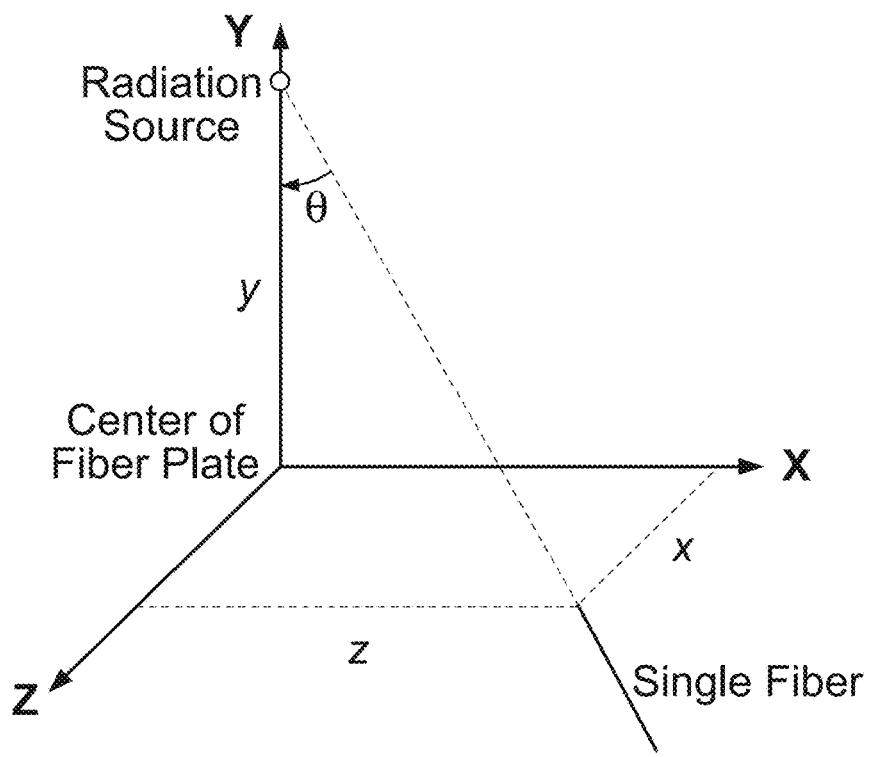

FIG. 8C shows the geometry for one fiber, where the center of the top fiber plate surface is at the origin, x and z are the distances of the fiber from the origin, and y is the radiation source (e.g., X-ray focal spot) distance from the origin. The tilt angle of each fiber, θ, is dependent of its (x, z) coordinates and is calculated by the following equation, $$\theta = \arctan\left(\frac{\sqrt{x^2+z^2}}{y}\right)$$

Figure 8D:
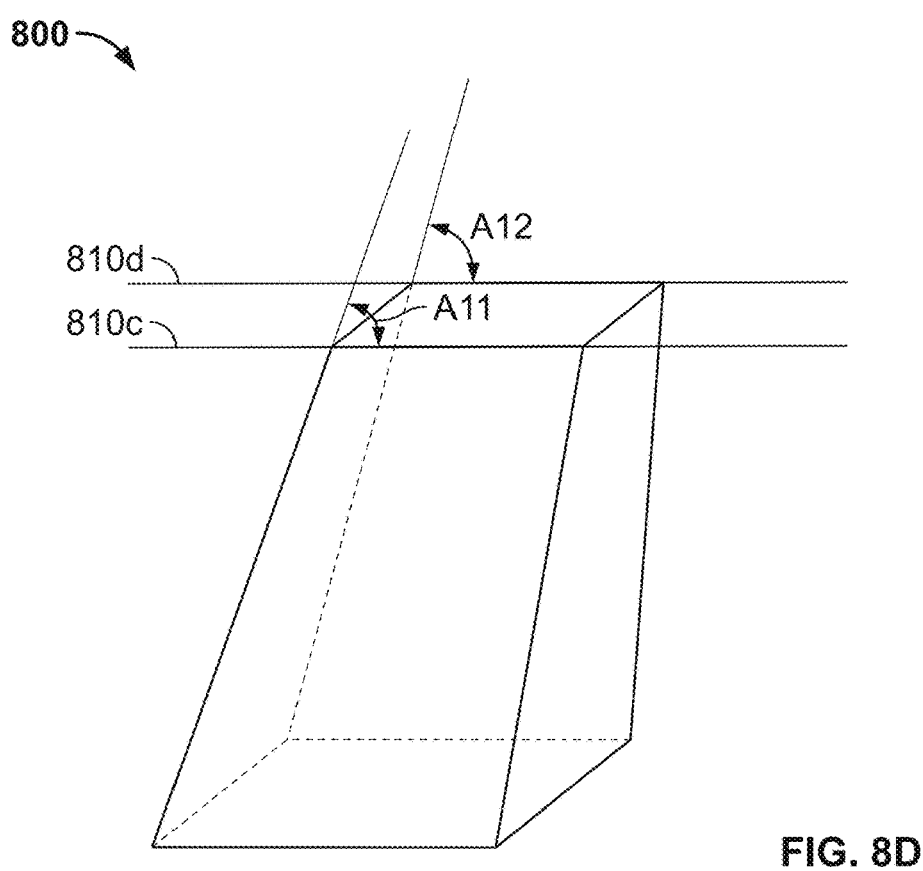

The method 820 may comprise creating 824 a top surface 805 by slicing along a first line 804 that transects across the fibers at an angle A7 (e.g., the tile face cut angle), creating 826 a bottom surface 807 by slicing along a second line 806 that transects across the fibers at an angle A8 and is parallel to the top surface 805 (i.e., angles A7 and A8 are substantially the same). Angles A7 and A8 may be selected in order for one or more fibers in the block to have a tilt angle A13 in accordance with Equation 1. The second line 806 may be a distance D2 away from the top surface 805. The method 820 may also comprise creating 828 a first side surface by slicing along a line 810a, which is at a tile cut angle A9 (which is the angle from a line that is normal to the top surface of the block), creating 830 a second side surface by slicing along a line 810b, which is at a tile cut angle A10, creating 832 a third side surface by slicing along a line 810c which transects the top and bottom surfaces at a tile cut angle A11, and creating 834 a fourth side surface by slicing along a line 810d which transects the top and bottom surfaces at a tile cut angle A12 (see FIG. 8D). The tilt cut angles A9-A12 may vary for each of the sides, depending on the location of the particular optical fiber block within the entire fiber optic plate, and the overall shape (e.g., trapezoidal or cuboid shape) of the fiber optic plate. In some variations, the tilt angle for any fiber within the fiber block may be determined at least in part by Equation 1. These steps may be repeated for each block of the plurality of blocks of the fiber optic plate, but the tile cut angles and tilt cut angles may vary for each of the blocks.

Figure 9A:
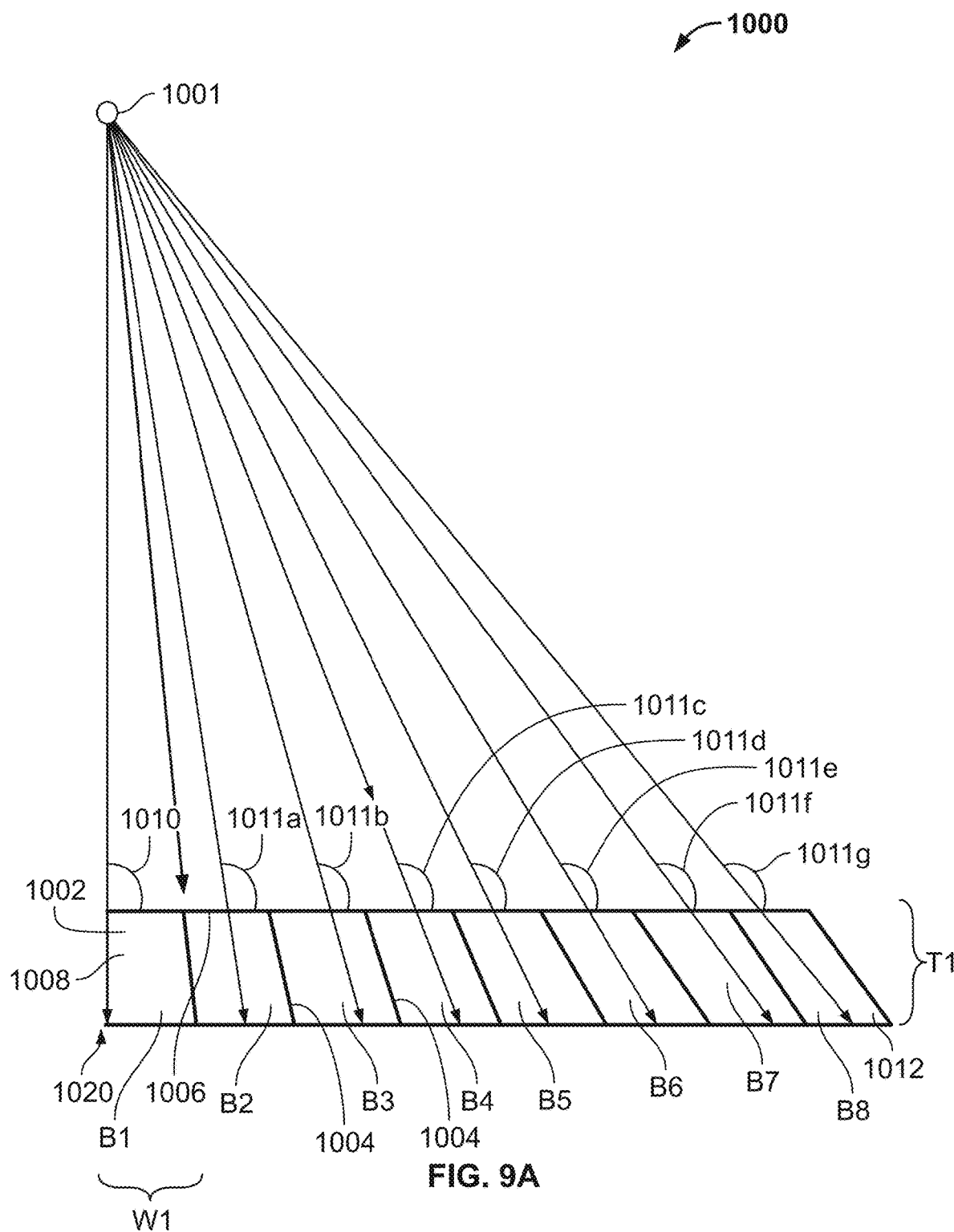
FIGS. 9A and 9B depict a first side schematic view of one variation of a fiber optic plate (along the X-direction) and FIG. 9C depicts Table 1, which summarizes the dimensions of the fiber optic plate depicted in FIGS. 9A and 9B.
Figures 9B, 9C:
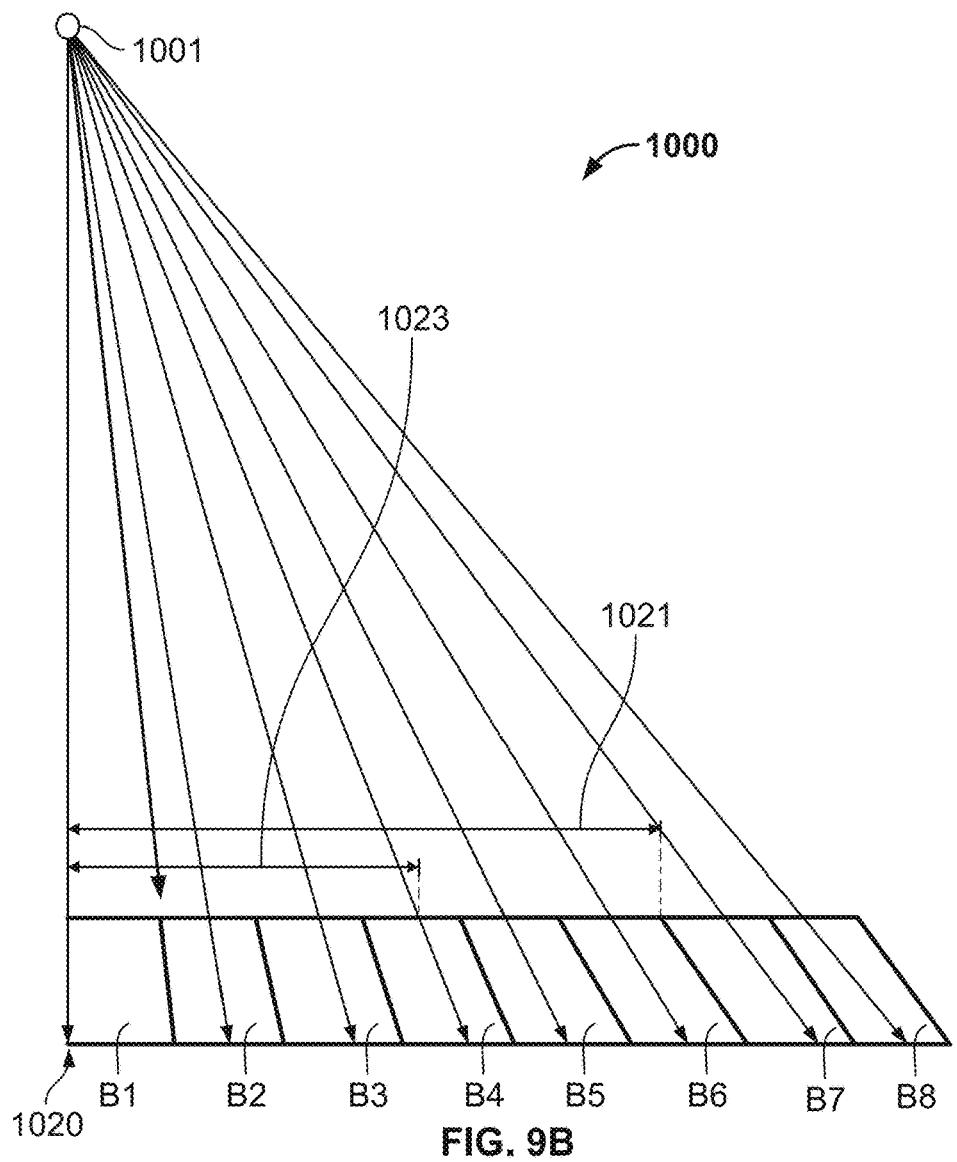
Figures 10A, 10B:
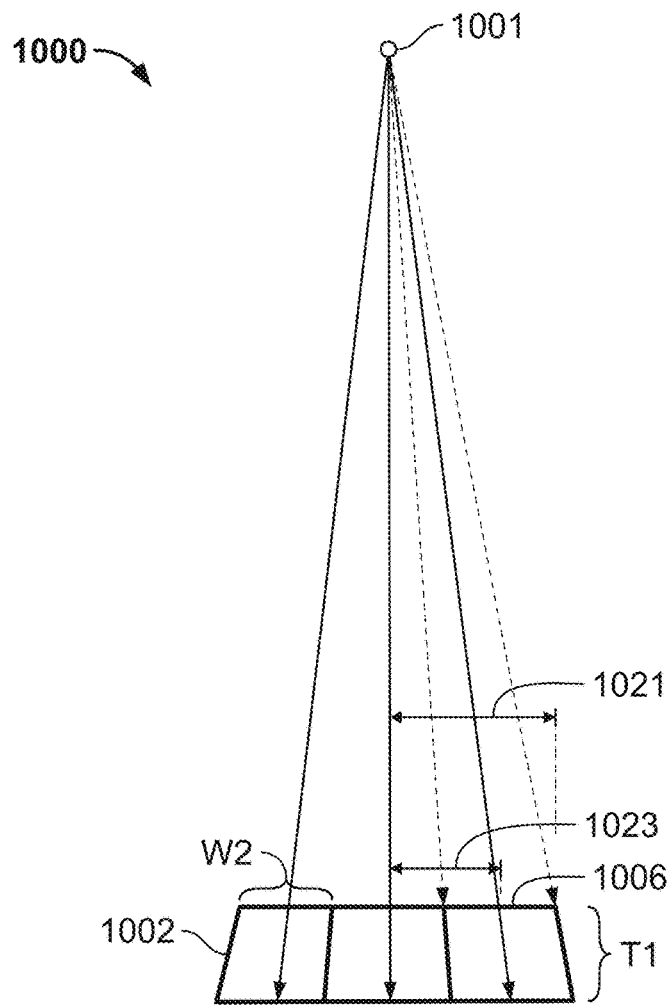
FIG. 10A depicts a second side schematic view (along the Z-direction) of the fiber optic plate of FIG. 9A.
FIG. 10B depicts Table 2, which summarizes the dimensions of a portion of one variation of a fiber optic plate depicted in FIG. 10A.

FIGS. 9A-9B and 10A-10B depict one example of a plurality of fiber optic blocks 1002 assembled together to form a fiber optic plate 1000 that may be focused to a radiation source 1001, which may be represented as a focal spot. FIG. 9A depicts one portion (e.g., the right half) of the fiber optic plate 1000 comprising assembled fiber blocks 1002 along the X-direction, FIG. 9C depicts a table (Table 1) that outlines example dimensions and angles of the portion of the fiber optic plate 1000 depicted in FIG. 9B (which is a reproduction of FIG. 9A for the purposes of clarity). The fiber optic plate 1000 may optionally comprise a low-Z layer or coating disposed over the top surface of the plate (e.g., the surface that faces the radiation source 1001), which may help to deflect low-energy, scattered X-rays, as described above. FIG. 10A depicts the fiber optic plate 1000 along the Z-direction and FIG. 10B depicts a table (Table 2) that outlines example dimensions and angles of the portion of the fiber optic plate 1000 depicted in FIG. 10A. The overall geometry of the fiber optic plate 1000 may be similar to that of the plate depicted in FIG. 1. This particular fiber optic plate 1000 may comprise eight blocks 1002 (numbered B1-B8) along the X-direction, with or without a thin sheet of heavy metal, which may be used as anti-scatter septa. Thin sheets of heavy metal may be located at the interface 1004 between each block 1002. Optionally, a thin sheet of metal may also be located along at least a portion of the top surface 1006 of the plate. The dimensions of each block may vary depending on the overall size of the fiber optic plate 1000. For example, the width W1 of each block B1-B8 along its bottom edge may be about 5.5 cm for an overall width in the x-direction of about 88 cm (about 44 cm for the left and right half). An MV detector with an overall width of about 88 cm may be used to detect the dose distribution and/or measure imaging data for a 6 MV radiation source located about 130 cm away from the detector, e.g., about 132.5 cm. The distance 1021 to the peripheral edge of each of the blocks B1-B8 from the central edge 1020 is summarized in Table 1. The distance 1023 to the block center from the central edge 1020 is also summarized in Table 1. The width W2 of each block along its top edge may be about 2.67 cm for an overall width in the z-direction of about 8 cm. The thickness T1 of the fiber optic plate may be about 5 cm. The left side blocks are symmetric and identical to the right side. The center block 1008 may have a fiber tilt angle 1010 of about 0 degrees and the tilt angle 1011a-1011g may progressively increase towards the end block 1012, where the fiber tilt angle in this angle is represented by the angle of the focused fibers of each fiber block relative to the top surface 1006. Examples of specific fiber tilt angles are also summarized in Table 1 of FIG. 9C. The blocks 1002 may be made from either the method depicted in FIGS. 7A-7C or the method depicted in FIGS. 8A-8D. The central fiber of each block may be focused to a radiation source, and/or the block may be fully focused, as previously described.

Radiation therapy systems that comprise the MV detectors described above may have at least two modes of operation. These modes of operation may be used in pre-treatment methods and/or may be used during and/or after treatment. A first mode of operation may be a "step-and-shoot" mode, where the gantry upon which the MV detector and radiation source are mounted is stationary during the imaging (e.g., not moving) and a single high dose projection image can be taken at a selected angle. The gantry can rotate to multiple angles and projection images can be taken from each angle. A second mode of operation may be a tomographic mode, where continuous low-dose, thin slices of image are taken while the gantry is rotating, i.e. the gantry is rotating while the MV detector is acquiring images. Both of these modes may be used for in a pre-treatment method for patient positioning. For pre-treatment imaging, the radiation source may emit a lower-energy beam (e.g., about 3 MV), which may result in an image with better contrast than using a high-energy beam (e.g., about 6 MV) which is used during treatment. While the MV detectors described herein may be used for dose measurements, in some systems, the data from the MV detectors may be used for imaging purposes, and may not necessarily be used for generating dose maps or images.

Figure 11B:
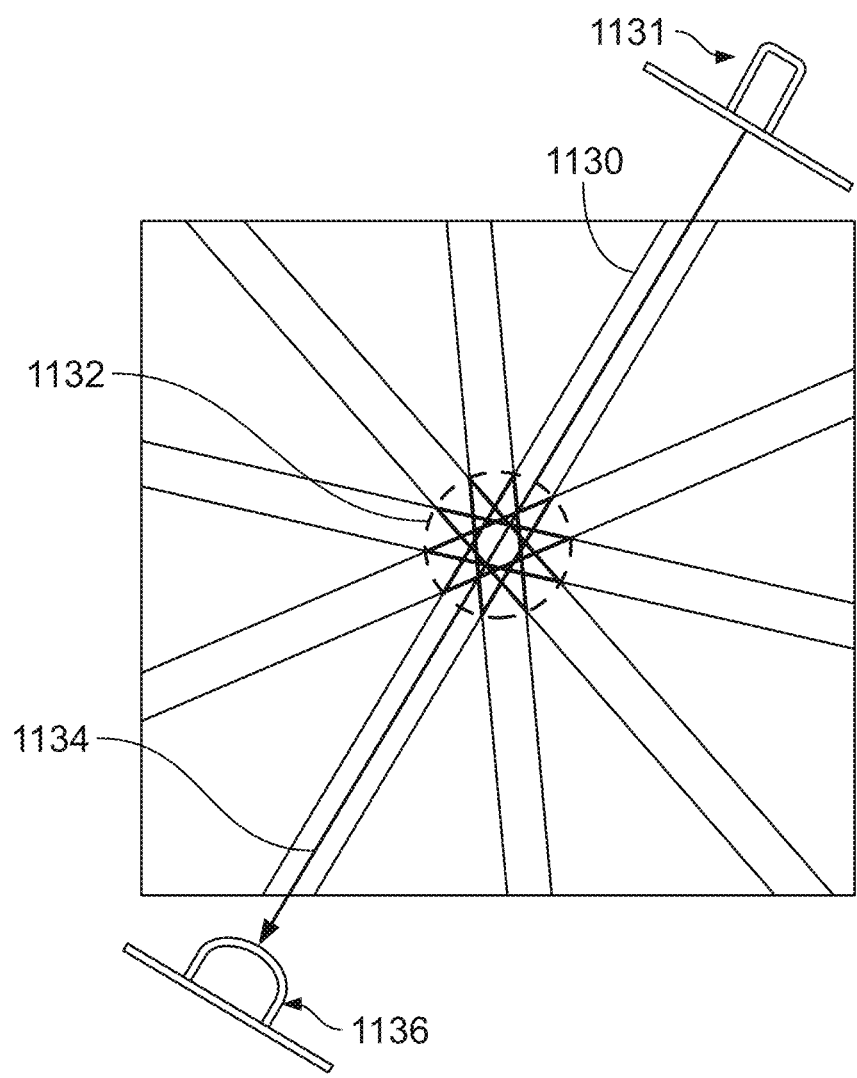
FIG. 11B schematically depicts entrance beams and exit beams for a plurality of gantry or firing angles.

During treatment, the MV detector may continuously measure the radiation that is transmitted through the patient (e.g., according to the timing depicted in FIG. 6). Based on the radiation applied by the radiation source and the radiation transmitted through the patient, the system controller may be configured to determine the radiation dose delivered or absorbed by the patient. In some variations, a method for radiation therapy may comprise moving the patient couch slowly through the patient region of the gantry while the gantry is rotating so that the radiation source emits radiation beams from multiple angles. The patient couch may move at very slow speed, for example about 0.07 mm/second. At this rate of movement, the helical pitch (couch-displacement per rotation/beam-width) is much smaller than 1 mm Table 3 depicted in FIG. 11A provides some example parameters (e.g., rates of rotation and movement) for one variation of a treatment session. Additional details regarding the computation of delivered dose are provided below and depicted in FIGS. 11B-C.

When the movement of the patient couch through the fan beam is significantly slower than the rate of gantry rotation, large portions of the slice may overlap each other. A slice is defined as the couch travel distance per rotation of the gantry. During the treatment session, the MV detector collects measurements of the radiation dose applied to the patient in-vivo and in real-time. That is, the MV detector measures the amount of radiation applied by the radiation source at each firing position around the gantry. For each firing position, the overlapped portion of the images can be summed and averaged. An anatomical region of interest may be imaged from the same angle multiple times during the slow couch motion. In each image, the anatomical region of interest may move at the same rate that the couch moves. These images may be shifted to overlap with each other. The overlapped images can then be summed and averaged. Such an image averaging scheme may help to improve signal-to-noise ratio (SNR). The averaging process can be carried out with an on-board computer, thereby reducing the amount of image data that needs to be transmitted to a remote computer and archived.

Figure 12A:
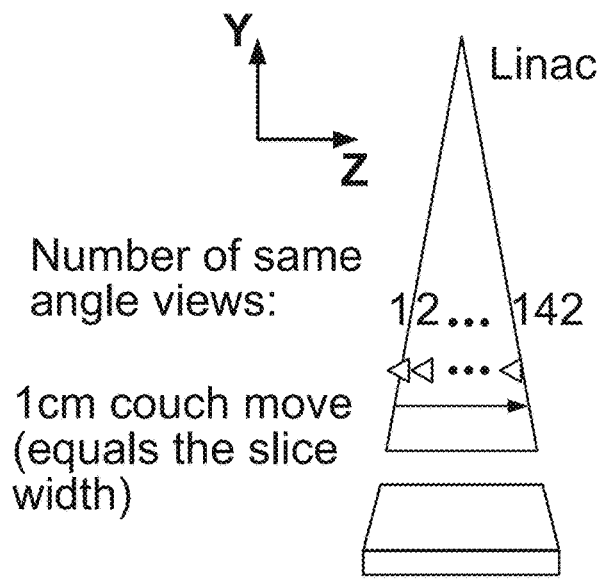
FIG. 12A is a graphical representation the same angle projection imaging of a moving fiducial marker (triangle) across the field of view, or the slice width, of an X-ray beam generated by the linac.
Figure 12B:
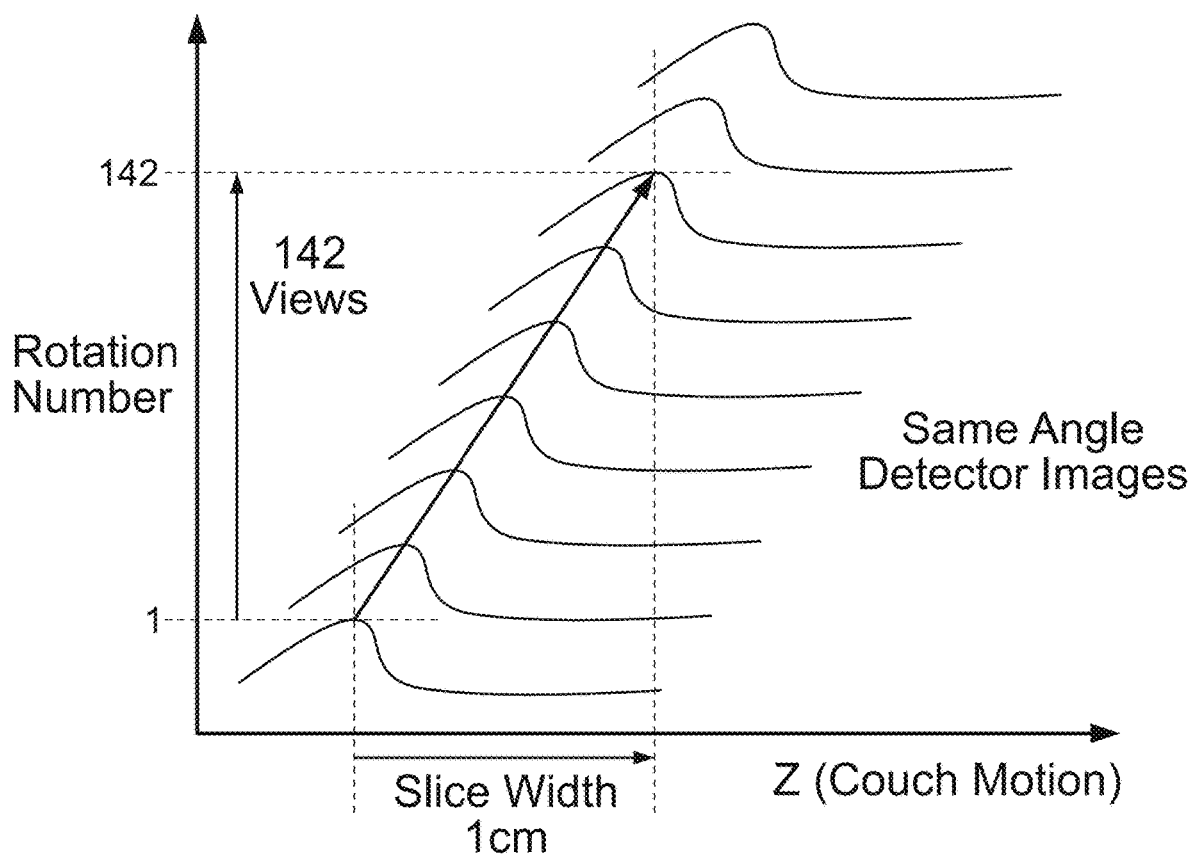
FIG. 12B is a shift-and-add graphical representation of one variation of an image and dose averaging scheme using the movement of the fiducial marker of FIG. 12A as an example.

One example of an image averaging scheme is illustrated in FIGS. 12A-12B and 13. In this example, the beam width is 8 mm, the lateral table movement per rotation (Z) is 0.07 mm/rotation, so the accumulated same-angle images are 8/0.07=114 rotations. Therefore 114 images can be averaged at any fixed angle of rotation. In this example, the SNR may improve by factor of 10.6, and image data volume may be reduced by factor of 114. In the example depicted in FIG. 12A, the slice width may be about 1 cm and couch displacement may be about 0.0704 mm per gantry rotation. During 1 cm of couch movement the gantry completes 142 rotations and for each rotation the MV detector acquires 100 projection images from the 100 firing angles. The MV detector may also acquire 142 view of the same anatomical slice, but shifted across the detector plane. FIG. 12B is a representation of a wave-shaped profile of projection images shifted across the detector plane. The images from the same gantry angle may be spatially shifted and overlapped with one other. The overlapped images may be averaged to improve the signal to noise ratios of the images. FIG. 13 is a graphical representation of the number of images available for averaging as a function of couch displacement for one variation of a radiation therapy system. The shaded areas show the start and end fringe regions. For first and the last centimeter (1 cm) of the couch movement, the number of images available for averaging will be less than 142 images. This is because the same angle views have not accumulated to maximum of 142.

Because the detector is made of water equivalent plastic materials, the dosimetric properties of the detector may facilitate dose calculation without the need for computationally-intensive corrections, as compared to the existing non-water equivalent EPID detectors. After a treatment session, a projection image may be generated from the dose calculation and combined with an anatomical image of the patient to generate a 3-D patient dose distribution image. In some variations, a controller of a radiation therapy system with any of the MV detectors described herein may be configured to generate a dose distribution map or image after a treatment session. For example, the radiation therapy system may be configured to acquire an anatomical image before the treatment session, acquire radiation dose data during the treatment session, process the radiation dose data (e.g., during or after the treatment session), and generate a composite image or map after the treatment session that comprises an overlay of the radiation dose distribution map or image over the pre-treatment anatomical image. Optionally, the radiation therapy system may acquire an anatomical image immediately after the treatment session and generate a composite image or map that comprises an overlay of the radiation dose distribution map or image over the post-treatment anatomical image. In some variations, the pre-treatment anatomical image and post-treatment anatomical image may be averaged together for the composite anatomical-dose distribution image. Alternatively, the radiation therapy system may be configured to generate a radiation dose distribution map or image, and not generate an anatomical image. Any anatomical images acquired by the radiation therapy system may be acquired using either (or both) 3 MV or 6 MV X-rays. For example, anatomical images acquired before or after the treatment session may be acquired using 3 MV X-rays, while any anatomical images acquired during the treatment session (e.g., when radiation beams for treatment are being applied to the patient) may be acquired using 6 MV X-rays.

Figure 11C:
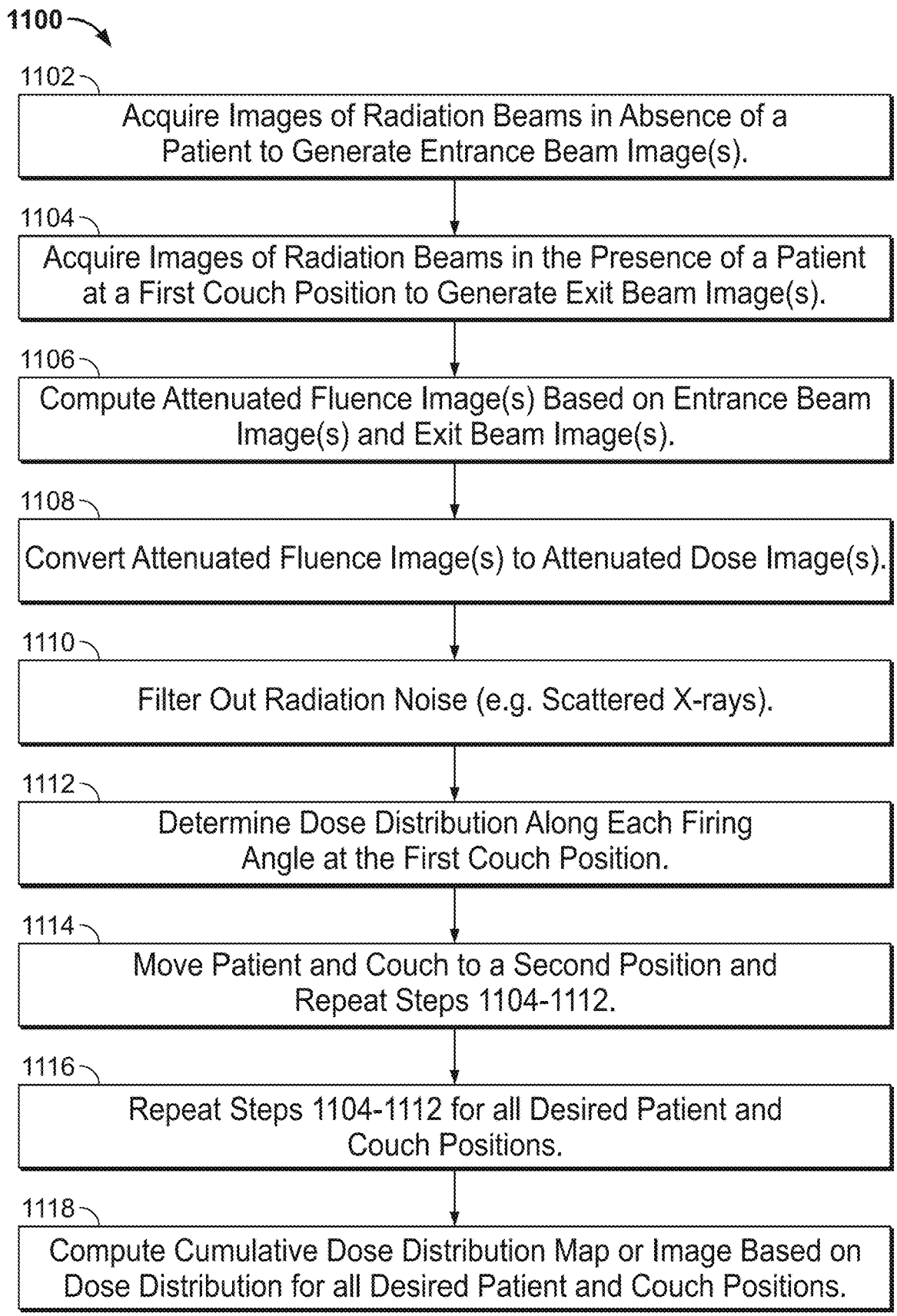
FIG. 11C is a flowchart depiction of one method for determining a dose distribution map or image using the MV detectors described herein.

One variation of a method for computing a dose map is depicted in FIG. 11C. The method 1100 may be used with a radiation therapy system that is configured to generate narrow beams (e.g., pencil beams) that are on the order of about 1 cm². Such narrow beams may be generated, for example, by collimating the output radiation of an X-ray source with a binary multi-leaf collimator (MLC). In some variations, the radiation therapy system may also comprise a rotatable gantry upon which the X-ray or radiation source is mounted and an MV detector (such as any of the variations described herein) disposed across from the X-ray source, such as the system depicted in FIG. 1A. The gantry may be rotatable about a patient area. Data from the MV detector may be stored and processed in a system controller comprising a microprocessor and computer-readable memory. In some variations, the steps of the method 1100 may be stored in a computer-readable memory as a pre-determined instruction set. In addition, the rotation of the gantry, firing of the X-ray or radiation source, MLC control, data output from the MV detector, including the timing related to these steps (e.g., firing and collimating radiation at certain gantry angles), may be carried out according to control signals originating from the system controller. The method 1100 may comprise the step 1102 of acquiring images of radiation beams in the absence of a patient (or a phantom) to generate entrance beam image(s). FIG. 11B schematically depicts an entrance beam 1130 as the radiation emitted by the X-ray or radiation source 1131 before it interacts with a patient or a phantom (which may be located in the region 1132 enclosed in dotted lines; in this particular depiction, there is no patient or phantom). Entrance beam images may include images of all the MLC single and multiple adjacent leaves simultaneously opening and may be acquired from a plurality of gantry or firing angles. The entrance beam image(s) may be acquired at one firing angle or at multiple firing angles. In some variations, the number of images may be reduced by limiting the number of adjacent leaves that can be opened during treatment (e.g., up to 6 adjacent leaves opening). Entrance beam image(s) may represent the X-ray fluence without any beam attenuation for each MLC leaf. The radiation incident upon the plane of the MV detector may be scaled to a patient entrance surface using, for example, the inverse radius square law.

After entrance beam images are generated, method 1100 may comprise the step 1104 of acquiring images of radiation beams in the presence of a patient (and/or a phantom) at a first couch position to generate exit beam image(s). Step 1104 may comprise loading a patient or phantom on a couch and advancing the couch into the patient area of the gantry. FIG. 11B schematically depicts an exit beam 1134 as the radiation that emerges from the patient (or phantom) that is incident on an MV detector 1136; i.e., radiation that has interacted with the patient or phantom. Step 1104 may be performed, for example, during a therapy session, and may include acquiring exit beam images of all the MLC single and multiple adjacent leaves simultaneously opening. The exit beam image(s) may be acquired at one firing angle or at multiple firing angles that correspond to the angles acquired in step 1102. In some variations, exit beam images may be averaged in order to reduce the number of images (for example, using the method depicted in FIGS. 12A-12B). The images of exit X-ray fluence from the patient may be recorded in vivo, i.e., in real time, by the MV detector for all the firing positions around the gantry. The exit beam images may be generated during couch movement, for example, as the couch moves in accordance with the parameters summarized in Table 3 of FIG. 11A. For example, the couch may move about 100 mm at a speed of about 0.07 mm/s. As explained previously, the total number of images (142857) may be reduced to 1000 by averaging the overlapped images. Alternatively or additionally, step 1104 may be executed while the couch is stopped at the first couch position.

After exit beam images are generated, method 1100 may comprise a step 1106 of computing attenuated fluence image(s) based on the entrance beam image(s) and exit beam image(s). In some variations, attenuated fluence image(s) (e.g., patient attenuated fluence images) may be generated by subtracting the averaged exit beam images of each corresponding leaves from the entrance beam leaf images.

Method 1100 may comprise the step 1108 of converting the attenuated fluence image(s) to attenuated dose image(s). The attenuated fluence images may be converted to attenuated dose images by empirical calibrations. One example of a calibration method may comprise placing dosimetric films (which may provide 2D dose images) in the same position of the MV detector imaging photodiode array plane. The film may be placed inside water or plastic phantoms with the same or equivalent thickness as the plastic FSFOP layer and the same back scatter layer. The film dose image and the MV detector fluence image may be acquired under the identical MV beam conditions (e.g., beam energy, attenuation layer, exposure time, etc.). The calibration method may further comprise creating correlation maps between the 2D MV detector fluence images and the corresponding the 2D film dose images. Because the MV detectors disclosed herein use low-Z, water-like scintillating materials, this conversion may be done without the complex calibration procedures used in for detectors (such as EPIDs) that comprise high-Z scintillation materials. Optionally, method 1100 may comprise the step 1110 of filtering out radiation noise (e.g., scatter correction). Scattered X-rays from the patient may create noise in the images and may cause errors in dose calculations. The amount of scatter may be proportional to the area irradiation by the radiation beam after it has been shaped by a collimator. In case of single leaf beam geometry (e.g., the beam is shaped by a multi-leaf collimator), the beam size may be less than few square centimeters (e.g., about 1 cm×0.625 cm or about 2 cm×0.625 cm at ISO), the scatter may be negligible and the scatter corrections may not be needed. For multiple leaf openings, scatter correction may help to improve the accuracy of the dose calculations. A scatter correction model may be created based on Monte Carlo simulations, or based on empirical scatter measurements, or combination of both.

Method 1100 may comprise the step of 1112 of determine the dose distribution along each firing angle (e.g., firing position) at the first couch position. For example, some systems may have about 100 firing positions around a gantry (e.g., a circular gantry), where each firing positions are about 36 degrees from each other. In some variations, the dose distribution may be computed by back projecting the exit dose image to patient dose along each firing angle for all opened leaves. The dose distribution along each firing angle may be computed using the preexisting data sets, which include PDD curves, beam geometry, energy spread kernel in the patient, and may optionally include data from patient CT images of attenuation coefficient numbers, i.e., CT numbers. A 2D patient dose may be calculated by the process of convolution and super position from all the firing angles in single slice. Notably, in this dose reconstruction method, the correction or calibration steps needed for the EPID dose images are not necessary, since the MV detectors here use low-Z scintillating fibers.

Method 1100 may comprise the step 1114 of moving the patient couch to a second position and repeating steps 1104-1112 at the second position (i.e., the second slice). Steps 1104-1112 may be repeated 1116 for all desired patient and couch positions. Method 1100 may comprise the step 1118 of computing a cumulative dose distribution map or image (which may be 3D) based on the dose distribution computations from steps 1104-1116 for all desired patient and couch positions. One of more of the steps of the method 1100 may be performed during a treatment session (e.g., while a patient is on the couch) and/or after a treatment session (e.g., after a patient has left the couch).

Although the foregoing systems, devices and methods have, for the purpose of clarity and understanding, been described in some detail by way of illustration and example, it will be apparent that certain changes and modifications may be practiced, and are intended to fall within the scope of the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described.

It must be noted that as used herein and in the appended claims, the singular forms "a", "an", and "the" include plural referents unless the context clearly dictates otherwise. Thus, for example, reference to "a block" includes a plurality of such blocks and reference to "the pixel" includes reference to one or more pixels and equivalents thereof known to those skilled in the art, and so forth.

The publications discussed herein are provided solely for their disclosure. Nothing herein is to be construed as an admission that the present invention is not entitled to ante-date such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

What is claimed:

1. A method of manufacturing an optical fiber plate comprising:
   providing a block of parallel scintillating optical fibers;
   slicing the block along a first axis that transects the optical fibers at a first angle with respect to the parallel fibers to create a top surface;
   slicing the block along a second axis that transects the optical fibers at a first distance away from the top surface to create a bottom surface, wherein the bottom surface is parallel to the top surface;
   slicing the block along a third axis to create a first side surface that is at a second angle with respect to the top surface; and
   slicing the block along a fourth axis at a second distance away from the third axis to create a second side surface, wherein the second side surface is at a third angle with respect to the top surface.

2. The method of claim 1, wherein the first distance is a thickness of an optical fiber plate and the second distance is a width of the optical fiber plate.

3. The method of claim 2, wherein the third angle is different from the second angle.

4. The method of claim 2, wherein the first angle is from about 10 degrees to about 180 degrees.

5. The method of claim 4, wherein the second and third angles are from about 0.5 degrees to about 40 degrees.

6. The method of claim 5, wherein the scintillating fiber located at the center of the optical fiber plate is at a fourth angle such that the center scintillating fiber is aligned with a ray of a radiation source fan beam located at a fixed distance away from the optical fiber plate.

7. The method of claim 1, further comprising slicing the block along a fifth axis to create a third side surface and a sixth axis at a third distance away from the fifth axis to create a fourth side surface, wherein the third side surface is at a fourth angle with respect to the top surface and the fourth side surface is at a fifth angle with respect to the top surface.

8. The method of claim 1, wherein the scintillating optical fibers comprise plastic scintillating optical fibers.

9. The method of claim 1, wherein the scintillating optical fibers have a diameter from about from about 5 μm to about 10 μm.

10. The radiation detector of claim 9, wherein the fiber diameter is about 10 μm.

11. A method of manufacturing an optical fiber plate comprising:
providing a billet of tapered scintillating optical fibers;
slicing the billet along a first axis that transects all of the fibers to create a top surface;
slicing the billet along a second axis that transects all of the fibers at a first distance away from the first cut to create a bottom surface, wherein the bottom surface is parallel to the top surface;
slicing the billet along a third axis to create a first side surface that is at a first angle with respect to the top surface; and
slicing the billet along a fourth axis at a second distance away from the third axis to create a second side surface that is at a second angle with respect to the top surface.

12. The method of claim 11, wherein the billet of scintillating optical fibers is thermally tapered.

13. The method of claim 11, wherein the taper angle of the billet of optical fibers is determined at least in part by the shape of a radiation beam from a radiation source that is to be located at a fixed distance away from the optical fiber plate.

14. The method of claim 11, wherein the first side surface extends along a length of a first boundary fiber in the tapered billet, and the second side surface extends along a length of a second boundary fiber in the tapered billet.

15. The method of claim 11, wherein the scintillating optical fibers comprise plastic scintillating optical fibers.

16. The method of claim 11, wherein the scintillating optical fibers have a diameter from about from about 5 μm to about 10 μm.

17. The radiation detector of claim 16, wherein the fiber diameter is about 10 μm.

* * * * *